(12) United States Patent
Guss et al.

(10) Patent No.: US 11,326,151 B2
(45) Date of Patent: May 10, 2022

(54) ENGINEERED MICROBES FOR CONVERSION OF ORGANIC COMPOUNDS TO MEDIUM CHAIN LENGTH ALCOHOLS AND METHODS OF USE

(71) Applicant: UT-Battelle, LLC, Oak Ridge, TN (US)

(72) Inventors: Adam M. Guss, Knoxville, TN (US); Joshua R. Elmore, Richland, WA (US); Jay D. Huenemann, Knoxville, TN (US)

(73) Assignee: UT-Battelle, LLC, Oak Ridge, TN (US)

(*) Notice: Subject to any disclaimer, the term of this patent is extended or adjusted under 35 U.S.C. 154(b) by 0 days.

(21) Appl. No.: 16/934,570

(22) Filed: Jul. 21, 2020

(65) Prior Publication Data

US 2021/0024960 A1 Jan. 28, 2021

Related U.S. Application Data

(60) Provisional application No. 62/876,882, filed on Jul. 22, 2019.

(51) Int. Cl.
*C12N 9/06* (2006.01)
*C12N 9/02* (2006.01)
(Continued)

(52) U.S. Cl.
CPC ............ *C12N 9/0008* (2013.01); *C12N 9/001* (2013.01); *C12N 1/20* (2013.01); *C12N 1/205* (2021.05);
(Continued)

(58) Field of Classification Search
CPC .......... C12N 9/001; C12N 9/0008; C12P 7/04
See application file for complete search history.

(56) References Cited

U.S. PATENT DOCUMENTS

| 9,708,630 B1 | 7/2017 | Pfleger et al. | |
|---|---|---|---|
| 2014/0127765 A1* | 5/2014 | Osterhout | C12N 9/88 435/134 |
| 2019/0330665 A1 | 10/2019 | Elmore et al. | |

OTHER PUBLICATIONS

Studer. Residue mutations and their impact on protein structure and function: detecting beneficial and pathogenic changes. Biochem. J. (2013) 449, 581-594.*

(Continued)

*Primary Examiner* — Yong D Pak
(74) *Attorney, Agent, or Firm* — Scully, Scott, Murphy & Presser, P.C.

(57) ABSTRACT

This disclosure provides a genetically-modified bacterium from the genus *Pseudomonas* that comprises an exogenous nucleic acid encoding an enoyl-CoA reductase and an exogenous nucleic acid encoding an acyl-CoA reductase that produces medium chain length alcohols. The disclosure further provides methods for producing medium chain alcohols using such genetically-modified bacterium. This disclosure provides a renewable, bio-based production platform for valuable mcl-alcohols that have a wide range of industrial applications. Current production of mcl-alcohols typically occurs through the hydrogenation of plant oils and waxes. This process leads to issues of deforestation and is largely unsustainable. Utilizing waste lignin streams as the carbon source provides a more sustainable feedstock that can be generated from plant waste like corn stover. Along with this, the use of lignin avoids competition with food resources as traditional starch and sugar feedstocks.

24 Claims, 4 Drawing Sheets

Specification includes a Sequence Listing.

(51) Int. Cl.
  *C12N 15/00* (2006.01)
  *C12N 1/20* (2006.01)
  *C12P 7/02* (2006.01)
  *C12P 7/04* (2006.01)
  *C12R 1/38* (2006.01)
  *C12R 1/185* (2006.01)

(52) U.S. Cl.
  CPC .......... *C12P 7/04* (2013.01); *C12R 2001/185* (2021.05); *C12R 2001/38* (2021.05)

(56) References Cited

OTHER PUBLICATIONS

Kim. Engineering of microbial cell factories for the sustainable production of fuels and chemicals uing a novel carbon elongation pathway. Doctor of Philosophy. Rice University. 2017.*
FABI_ECOLI. UniProtKB Database. Mar. 2018.*
Wang. Development of a New Strategy for Production of Medium-Chain-Length Polyhydroxyalkanoates by Recombinant *Escherichia coli* via Inexpensive Non-Fatty Acid Feedstocks. Applied and Environmental Microbiology p. 519-527. Nov. 18, 2011.*
A1U3L3_MARHV. UniProtKB Database. Apr. 2018.*
Mehrer. Anaerobic Production of Medium-Chain Fatty Alcohols via a β-Reduction Pathway Metab Eng. Jul. 2018; 48: 63-71. Published online May 25, 2018.*
Clomburg, J. et al., "Biofuel production in *Escherichia coli*: the role of metabolic engineering and synthetic biology", Applied Microbiology and Biotechnology, 86(2): 419-434 (2010).
Diender, M. et al., "Production of medium-chain fatty acids and higher alcohols by a synthetic co-culture grown on carbon monoxide or syngas", Biotechnology for Biofuels, vol. 9, article 82, pp. 1-11 (2016).
Hamilton-Kemp, T. et al., "Production of the Long-Chain Alcohols Octanol, Decanol, and Dodecanol by *Escherichia coli*", Current Microbiology, 51(2): 82-86 (2005).
Henritzi, S. et al., "An engineered fatty acid synthase combined with a carboxylic acid reductase enables de novo production of 1-octanol in Saccharomyces cerevisiae", Biotechnology for Biofuels, vol. 11, article 150, pp. 1-12 (2018).
Liu, A. et al., "Fatty alcohol production in engineered *E. coli* expressing Marinobacter fatty acyl-CoA reductases", Applied Microbiology and Biotechnology, 97(15): 7061-7071 (2013).
Rutter, C. D. et al., "Production of 1-decanol by metabolically engineered Yarrowia lipolytica", Metabolic Engineering, 38: 139-147 (2016).
Xu, P. et al., "Engineering Yarrowia lipolytica as a platform for synthesis of drop-in transportation fuels and oleochemicals", Proceedings of the National Academy of Sciences, 113(39): 10848-10853 (2016).
Youngquist, J. T. et al., "Production of medium chain length fatty alcohols from glucose in *Escherichia coli*", Metabolic Engineering, 20: 177-186 (2013).

* cited by examiner

ENGINEERED MICROBES FOR CONVERSION OF ORGANIC COMPOUNDS TO MEDIUM CHAIN LENGTH ALCOHOLS AND METHODS OF USE

CROSS REFERENCE TO RELATED APPLICATION

This application claims the benefit of priority from U.S. Provisional Application No. 62/876,882, filed Jul. 22, 2019, the contents of which are incorporated herein by reference.

STATEMENT REGARDING FEDERALLY SPONSORED RESEARCH OR DEVELOPMENT

This disclosure was made with government support under a research project supported by Prime Contract No. DE-AC05-00OR22725 awarded by the U.S. Department of Energy. The government has certain rights in this invention.

INCORPORATION BY REFERENCE OF SEQUENCE LISTING

The Sequence Listing in the ASCII text file, named as 38426_4425.1_Seqlist_ST25.txt of 115 KB, created on Jul. 20, 2020, and submitted to the United States Patent and Trademark Office via EFS-Web, is incorporated herein by reference.

BACKGROUND

Lignin is the second most abundant carbon-based polymer found in nature; however, it is currently underutilized as a resource due to its chemical complexity and recalcitrance. The conversion of lignin derived carbon into value-added products is essential to support the economic viability of lignocellulosic refineries targeting the production of biofuels from lignocellulose derived sugars. Typically treated as waste and burned for process heat, the utilization of lignin streams offers a low-cost carbon source that can be utilized in place of traditional, more expensive feedstocks for bioprocesses. The valorization of lignin can be difficult, though an emerging solution to this challenge is the use of bacteria to convert depolymerized lignin into value added products. The United States can generate 1.3 billion dry tons of lignocellulosic biomass annually without competing with food crops for land use, and hence potentially deliver an equivalent supply of 3.8 billion barrels of oils that can replace more than 50% of liquid transportation derived from fossil fuels. However, one major limitation is that lignocellulosic residuals (i.e., lignins) constituting about 30% of the total biomass content cannot be currently used for fermentation and are underused as a low-value heating source by biorefinery processes. Therefore, it is significant to develop enabling technologies for transformation of this underused biomass source into high-value chemicals, biofuels, and biomaterials.

Utilization of the effluent lignocellulose waste stream would improve the overall process efficiency of second-generation biofuel production because the additional product would offset operating costs. This would effectively decrease the cost of the ethanol or butanol products, making them more competitive with traditional fossil fuels.

Medium chain length alcohols (mcl-alcohols) can be employed as bio-based fuel additives with competitive advantages over traditional biofuel additives like ethanol. Ethanol is very hygroscopic and can therefore induce spoiling of gasoline and corrosion of fuel storage systems. Mcl-alcohols are more hydrophobic and therefore reduce the risks of fuel spoilage and corrosion. Further, the energy density of these alcohols is higher than that of shorter chain biofuels. This allows for similar energy yields in smaller volumes when compared to ethanol. These advantages make mcl-alcohols a promising alternative to conventional biofuel additives. Beyond the biofuel market, fatty alcohols are also used in a variety of industries as solvents and surfactants, and as additives in creams and cosmetics. These industrial applications present an initial market that can be exploited for increasing the value of the mcl-alcohol products. Current methods to produce fatty alcohols industrially are through the hydrogenation of oils and waxes derived from plants. This process incurs high environmental costs that stem from increased deforestation to obtain the oil from palm fruits.

SUMMARY OF THE DISCLOSURE

In one aspect, the disclosure provides a genetically-modified bacterium from the genus *Pseudomonas*, comprising an exogenous nucleic acid encoding an enoyl-CoA reductase and an exogenous nucleic acid encoding an acyl-CoA reductase.

In some embodiments, the enoyl-CoA reductase encoded by the exogenous nucleic acid is an enzyme from a bacterium that is not *Pseudomonas*. In some embodiments, the enoyl-CoA reductase is an enzyme from a bacterial species that belongs to the genus *Escherichia*. In some embodiments, the enoyl-CoA reductase comprises an amino acid sequence with at least about 90% identity to SEQ ID NO: 1. In some embodiments, the enoyl-CoA reductase is an enzyme from a single cell flagellate eukaryote species that belongs to the genus *Euglena*. In some embodiments, the enoyl-CoA reductase comprises an amino acid sequence with at least about 90% identity to SEQ ID NO: 5. In some embodiments, the exogenous nucleic acid encoding an enoyl-CoA reductase is codon optimized for the species of the genus *Pseudomonas* to which the genetically modified bacterium belongs.

In some embodiments, the acyl-CoA reductase is an enzyme from a proteobacterial species that belongs to the genus *Marinobacter*. In some embodiments, the acyl-CoA reductase comprises an amino acid sequence with at least about 90% identity to SEQ ID NO: 3. In some embodiments, the exogenous nucleic acid encoding an acyl-CoA reductase is codon optimized for the species of the genus *Pseudomonas* to which the genetically modified bacterium belongs.

In some embodiments, the endogenous genes that encode polyhydroxyalkanoates (PHA) synthases are mutated to be inactivated in the bacterium.

In some embodiments, the endogenous genes that encode fatty acid degradation enzymes are mutated to be inactivated in the bacterium.

In some embodiments, the endogenous genes that encode PQQ-dependent alcohol dehydrogenase enzymes are mutated to be inactivated in the bacterium.

In some embodiments, the exogenous nucleic acid encoding an enoyl-CoA reductase and the exogenous nucleic acid encoding an acyl-CoA reductase are placed in the same vector. In some embodiments, the exogenous nucleic acid encoding an enoyl-CoA reductase and the exogenous nucleic acid encoding an acyl-CoA reductase are placed in separate vectors.

In some embodiments, the bacterium is selected from the group consisting of *P. aeruginosa, P. alcaligenes, P. anguilliseptica, P. argentinensis, P. borborid, P. citronellolis, P.*

*flavescens, P. mendocina, P. nitroreducens, P. oleovorans, P. pseudoalcaligenes, P. resinovorans, P. straminea, P. asplenii, P. aurantiaca, P. aureofaciens, P. chlororaphis, P. corrugate, P. fragi, P. lundensis, P. taetrolens, P. antarctica, P. azotoformans, P. blatchfordae, P. brassicacearum, P. brenneri, P. cedrina, P. corrugate, P. fluorescens, P. gessardii, P. libanensis, P. mandelii, P. marginalis, P. mediterranea, P. meridiana, P. migulae, P. mucidolens, P. orientalis, P. panacis, P. protegens, P. proteolytica, P. rhodesiae, P. synxantha, P. thivervalensis, P. tolaasii, P. veronii, P. denitrificans, P. pertucinogena, P. putida group, P. cremoricolorata, P. entomophila, P. fulva, P. monteilii, P. mosselii, P. oryzihabitans, P. parafulva, P. plecoglossicida, P. putida, P. balearica, P. luteola, P. stutzeri, P. amygdali, P. avellanae, P. caricapapayae, P. cichorii, P. coronafaciens, P. ficuserectae, P. helianthin, P. meliae, P. savastanoi, P. syringae, P. tomato, P. viridiflava, P. abietaniphila, P. acidophila, P. agarici, P. alcaliphila, P. alkanolytica, P. amyloderamosa, P. asplenii, P. azotifigens, P. cannabina, P. coenobios, P. congelans, P. costantinii, P. cruciviae, P. delhiensis, P. excibis, P. extremorientalis, P. frederiksbergensis, P. fuscovaginae, P. gelidicola, P. grimontii, P. indica, P. jessenii, P. jinjuensis, P. kilonensis, P. knackmussii, P. koreensis, P. lini, P. lutea, P. moraviensis, P. otitidis, P. pachastrellae, P. palleroniana, P. papaveris, P. peli, P. perolens, P. poae, P. pohangensis, P. protegens, P. psychrophile, P. psychrotolerans, P. rathonis, P. reptilivora, P. resiniphila, P. rhizosphaerae, P. rubescens, P. salomonii, P. segitis, P. septica, P. simiae, P. suis, P. teessidea, P. thermotolerans, P. toyotomiensis, P. tremae, P. trivialis, P. turbinellae, P. tuticorinensis, P. umsongensis, P. vancouverensis, P. vranovensis, P. xanthomarina*, and *P. taiwanensis*.

Another aspect of the disclosure is directed to a method for converting an organic compound to a medium chain length alcohol, the method comprising inoculating a medium comprising said organic compound with the genetically-modified bacterium disclosed herein, thereby converting said organic compound to a medium chain length alcohol.

In some embodiments, the enoyl-CoA reductase encoded by the exogenous nucleic acid is an enzyme from a bacterium that is not *Pseudomonas*. In some embodiments, the enoyl-CoA reductase is an enzyme from a bacterial species that belongs to the genus *Escherichia*. In some embodiments, the enoyl-CoA reductase comprises an amino acid sequence with at least about 90% identity to SEQ ID NO: 1. In some embodiments, the enoyl-CoA reductase is an enzyme from a single cell flagellate eukaryote species that belongs to the genus *Euglena*. In some embodiments, the enoyl-CoA reductase comprises an amino acid sequence with at least about 90% identity to SEQ ID NO: 5. In some embodiments, the exogenous nucleic acid encoding an enoyl-CoA reductase is codon optimized for the species of the genus *Pseudomonas* to which the genetically modified bacterium belongs.

In some embodiments, the acyl-CoA reductase is an enzyme from a proteobacterial species that belongs to the genus *Marinobacter*. In some embodiments, the acyl-CoA reductase comprises an amino acid sequence with at least about 90% identity to SEQ ID NO: 3.

In some embodiments, the exogenous nucleic acid encoding an acyl-CoA reductase is codon optimized for the species of the genus *Pseudomonas* to which the genetically modified bacterium belongs.

In some embodiments, the endogenous genes that encode polyhydroxyalkanoates (PHA) synthases are mutated to be inactivated in the bacterium.

In some embodiments, the endogenous genes that encode fatty acid degradation enzymes are mutated to be inactivated in the bacterium.

In some embodiments, the endogenous genes that encode PQQ-dependent alcohol dehydrogenase enzymes are mutated to be inactivated in the bacterium.

In some embodiments, the organic compound comprises a carbon source. In some embodiments, the carbon source comprises a breakdown product of lignin. In some embodiments, the breakdown product of lignin comprises p-coumaric acid, ferulic acid, or saccharides.

In some embodiments, the medium comprises a limited quantity of an essential nutrient. In some embodiments, the essential nutrient is nitrogen. In some embodiments, the ratio of the amount of the carbon to the amount of the nitrogen in the media is about 25:4.

In some embodiments, the exogenous nucleic acid encoding an enoyl-CoA reductase and the exogenous nucleic acid encoding an acyl-CoA reductase are placed in the same vector.

In some embodiments, the exogenous nucleic acid encoding an enoyl-CoA reductase and the exogenous nucleic acid encoding an acyl-CoA reductase are placed in separate vectors.

In some embodiments, bacterium is selected from the group consisting of *P. aeruginosa, P. alcaligenes, P. anguilliseptica, P. argentinensis, P. borborid, P. citronellolis, P. flavescens, P. mendocina, P. nitroreducens, P. oleovorans, P. pseudoalcaligenes, P. resinovorans, P. straminea, P. asplenii, P. aurantiaca, P. aureofaciens, P. chlororaphis, P. corrugate, P. fragi, P. lundensis, P. taetrolens, P. antarctica, P. azotoformans, P. blatchfordae, P. brassicacearum, P. brenneri, P. cedrina, P. corrugate, P. fluorescens, P. gessardii, P. libanensis, P. mandelii, P. marginalis, P. mediterranea, P. meridiana, P. migulae, P. mucidolens, P. orientalis, P. panacis, P. protegens, P. proteolytica, P. rhodesiae, P. synxantha, P. thivervalensis, P. tolaasii, P. veronii, P. denitrificans, P. pertucinogena, P. putida group, P. cremoricolorata, P. entomophila, P. fulva, P. monteilii, P. mosselii, P. oryzihabitans, P. parafulva, P. plecoglossicida, P. putida, P. balearica, P. luteola, P. stutzeri, P. amygdali, P. avellanae, P. caricapapayae, P. cichorii, P. coronafaciens, P. ficuserectae, P. helianthin, P. meliae, P. savastanoi, P. syringae, P. tomato, P. viridiflava, P. abietaniphila, P. acidophila, P. agarici, P. alcaliphila, P. alkanolytica, P. amyloderamosa, P. asplenii, P. azotifigens, P. cannabina, P. coenobios, P. congelans, P. costantinii, P. cruciviae, P. delhiensis, P. excibis, P. extremorientalis, P. frederiksbergensis, P. fuscovaginae, P. gelidicola, P. grimontii, P. indica, P. jessenii, P. jinjuensis, P. kilonensis, P. knackmussii, P. koreensis, P. lini, P. lutea, P. moraviensis, P. otitidis, P. pachastrellae, P. palleroniana, P. papaveris, P. peli, P. perolens, P. poae, P. pohangensis, P. protegens, P. psychrophile, P. psychrotolerans, P. rathonis, P. reptilivora, P. resiniphila, P. rhizosphaerae, P. rubescens, P. salomonii, P. segitis, P. septica, P. simiae, P. suis, P. teessidea, P. thermotolerans, P. toyotomiensis, P. tremae, P. trivialis, P. turbinellae, P. tuticorinensis, P. umsongensis, P. vancouverensis, P. vranovensis, P. xanthomarina*, and *P. taiwanensis*.

DETAILED DESCRIPTION OF THE DISCLOSURE

Definitions

Figure 1:
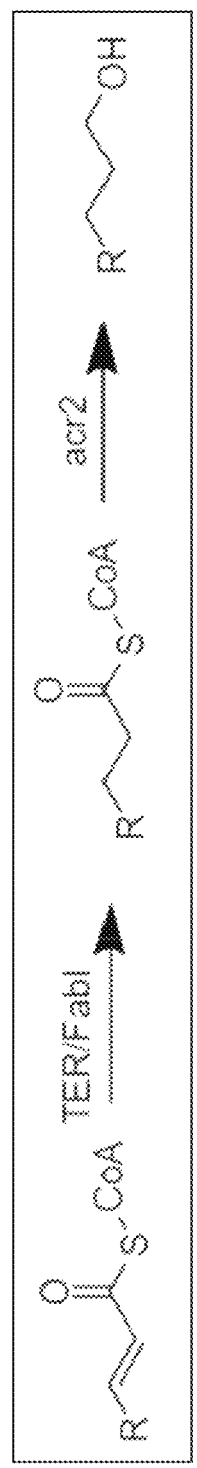
FIG. 1. Medium chain length (mcl) Alcohol Production Pathway. Schematic of two step production pathway from carbon metabolism intermediates. Initial reduction from enoyl-CoA β-oxidation intermediate catalyzed by transenoyl-CoA reductase (TER/FabI). Terminal reduction to mcl-alcohol catalyzed by acyl-CoA reductase (acr2).

As used herein, the term "about" refers to an approximately ±10% variation from a given value.

The term "cellulose" (also "lignocellulose" or "cellulosic substrate") refers to a structural material that comprises much of the mass of plants. Lignocellulose is composed mainly of carbohydrate polymers (cellulose, hemicelluloses) and an aromatic polymer (lignin).

The term "codon-optimized" refers to nucleic acid molecules that are modified based on the codon usage of the host species (e.g., a specific *Pseudomonas* species used), but without altering the polypeptide sequence encoded by the nucleic acid.

As used herein, the term "fermentation" refers to the enzymatic and/or anaerobic breakdown of organic substances by microorganisms to produce simpler organic compounds such as alcohols. While fermentation may occur under anaerobic conditions, it is not intended that the term be solely limited to strict anaerobic conditions, as fermentation may also occur under aerobic (e.g., in the presence of oxygen) or microaerobic conditions.

The term "genetically engineered" or "genetically modified" used in connection with a microorganism means that the microorganism comprises a genome that has been modified (e.g., one or more nucleotides have been added, deleted or substituted relative to the original or natural-occurring genome of the microorganism), or the microorganism comprises an exogenously introduced nucleic acid.

"Lignin", as used herein, refers to a complex polymer composed of monolignol subunits, primarily syringyl (S), guaiacyl (G) and p-hydroxyphenyl (H) monolignols, derived from sinapyl, coniferyl and p-coumaryl alcohols, respectively. Differences in the ratio of monolignols, and differences in expression and/or activity of lignin biosynthetic anabolic enzymes, create considerable variability in lignin structures, which differ between species, within species, within different tissues of a single plant and even within a single plant cell.

As used herein, a "medium chain length alcohol" or an "mcl-alcohol" refers to an aliphatic alcohol that contains between 8-16 carbons. Examples of mcl-alcohols include octanol (8 carbons—C8), decanol (10 carbons—C10), dodecanol (twelve carbons—C12), tetradecanol (14 carbons—C14), and hexadecanol (16 carbons—C16).

Disclosed herein are a genetically-modified bacterium from the genus *Pseudomonas* that can produce medium chain length alcohols (mcl-alcohols) and methods of producing mcl-alcohols using the disclosed genetically-modified bacterium.

Genetically-Modified Bacterium

In some embodiments, the present disclosure is directed to a genetically-modified bacterium from the genus *Pseudomonas* comprising an exogenous nucleic acid encoding an enoyl-CoA reductase and an exogenous nucleic acid encoding an acyl-CoA reductase.

As used herein, an "enoyl-CoA reductase" or "trans-2-enoyl-CoA reductase" refers to an enzyme that catalyzes reduction of enoyl-CoA to acyl-CoA. In some embodiments, an enoyl-CoA reductase is a non-endogenous (or "heterologous") enzyme. As used in this disclosure, the term "non-endogenous enzyme" refers to an enzyme that is from a species other than the host bacterium. The use of non-endogenous enzyme has advantages because a non-endogenous enzyme expressed from an exogenous nucleic acid is not under the regulatory restrictions of an endogenous enzyme, including, but not limited to, transcriptional, post-transcriptional and allosteric regulation. In some embodiments, the enoyl-CoA reductase is an enzyme from a bacterial species that is not *Pseudomonas*. In some embodiments, the enoyl-CoA reductase is an enzyme from a bacterial species that belongs to the genus *Escherichia*. In a specific embodiment, the enoyl-CoA reductase enzyme is encoded by the fabI gene from *E. coli*. In some embodiments, the enoyl-CoA reductase comprises a amino acid sequence with at least about 90% identity, at least 95% identity, at least 98% identity, at least 99% or greater identity to SEQ ID NO: 1. In some embodiments, the enoyl-CoA reductase is an enzyme from a single cell flagellate eukaryote species that belongs to the genus *Euglena*. In a specific embodiment, the enoyl-CoA reductase enzyme is encoded by the ter gene from *Euglena gracilis*. In some embodiments, the enoyl-CoA reductase comprises an amino acid sequence with at least about 90% identity, at least 95% identity, at least 98% identity, at least 99% or greater identity to SEQ ID NO: 5. In some embodiments, the exogenous nucleic acid encoding an enoyl-CoA reductase is codon optimized for the species of the genus *Pseudomonas* to which the genetically modified bacterium belongs.

As used herein, an "acyl-CoA reductase" or "fatty acyl-CoA reductase" refers to an enzyme that catalyzes the reduction of fatty acyl-CoA to fatty alcohols. In some embodiments, the fatty alcohols comprise medium chain length alcohols. In some embodiments, the acyl-CoA reductase used in the present disclosure is able to catalyze the two-step reduction from acyl-CoA to alcohol without producing intermediate free fatty aldehydes that are toxic to bacteria. In some embodiments, the acyl-CoA reductase is an enzyme from a proteobacterial species that belongs to the genus *Marinobacter*. In a specific embodiment, the acyl-CoA reductase enzyme is encoded by the acr2 gene from *M. aquaeolei*. In some embodiments, the acyl-CoA reductase comprises an amino acid sequence with at least about 90% identity, at least 95% identity, at least 98% identity, at least 99% or greater identity to SEQ ID NO: 3. In some embodiments, the exogenous nucleic acid encoding an acyl-CoA reductase is codon optimized for the species of the genus *Pseudomonas* to which the genetically modified bacterium belongs.

In some embodiments, the exogenous nucleic acid encoding an enoyl-CoA reductase and the exogenous nucleic acid encoding an acyl-CoA reductase are placed in the same vector. In some embodiments, enoyl-CoA reductase and acyl-CoA reductase enzymes are expressed from the same vector. In some embodiments, the exogenous nucleic acid encoding an enoyl-CoA reductase and the exogenous nucleic acid encoding an acyl-CoA reductase are placed in separate vectors. In some embodiments, the exogenous nucleic acid encoding an enoyl-CoA reductase and the exogenous nucleic acid encoding an acyl-CoA reductase are integrated into the genome of the bacterium. In some embodiments, the exogenous nucleic acid encoding an enoyl-CoA reductase and the exogenous nucleic acid encoding an acyl-CoA reductase are not integrated into the genome of the bacterium, e.g., remain on a vector such as a plasmid.

In some embodiments, an endogenous gene encoding for a poly-hydroxyalkonate (PHA) synthase enzyme is mutated to be inactivated in the bacterium. In some embodiments, all poly-hydroxyalkonate synthase enzymes are mutated to be inactivated in the bacterium. In a specific embodiment, the endogenous phaC1 gene and the endogenous phaC2 gene are inactivated in the bacterium.

In some embodiments, the inactivation of a poly-hydroxyalkonate synthase gene includes a deletion of the whole or a part of the gene such that no functional protein product is expressed (also known as gene knock out). The inactivation of a poly-hydroxyalkonate gene may include a deletion of the promoter or the coding region, in whole or in part, such that no functional protein product is expressed. In other embodiments, the inactivation of a poly-hydroxyalkonate synthase gene includes introducing an inactivating mutation to the gene, such as an early STOP codon in the coding sequence of the gene, such that no functional protein product is expressed. In some embodiments, the inactivation of a poly-hydroxyalkonate synthase gene includes introducing a mutation to the gene that will eliminate the enzymatic activity of the poly-hydroxyalkonate synthase protein (i.e., synthesis of polyhydroxyalkanoates (PHA)).

In some embodiments, a gene that encodes a fatty acid degradation enzyme is mutated to be inactivated in the bacterium. In some embodiments, all genes that encode fatty acid degradation enzymes are mutated to be inactivated in the bacterium. In a specific embodiment, one, more or all of the endogenous fadBA, fadAxBxEx, fadE, and qedHI/II genes are mutated to be inactivated in the bacterium. In some embodiments, the fatty acid degradation enzyme comprises a Pyrroloquinoline quinine (PQQ)-dependent alcohol dehydrogenase. In some embodiments, all endogenous genes that encode PQQ-dependent alcohol dehydrogenases are mutated to be inactivated in the bacterium.

In some embodiments, the inactivation of a fatty acid degradation enzyme gene includes a deletion of the whole or a part of the gene such that no functional protein product is expressed (also known as gene knock out). The inactivation of a fatty acid degradation enzyme gene may include a deletion of the promoter or the coding region, in whole or in part, such that no functional protein product is expressed. In other embodiments, the inactivation of fatty acid degradation enzyme gene includes introducing an inactivating mutation to the gene, such as an early STOP codon in the coding sequence of the gene, such that no functional protein product is expressed. In some embodiments, the inactivation of the fatty acid degradation enzyme gene includes introducing a mutation to the gene that will eliminate the enzymatic activity of the protein (i.e., degradation of fatty acids).

In some embodiments, gene inactivation is achieved using available gene targeting technologies in the art. Examples of gene targeting technologies include the Cre/Lox system (described in Kühn, R., & M. Tones, R., *Transgenesis Techniques: Principles and Protocols*, (2002), 175-204.), homologous recombination (described in Capecchi, Mario R., *Science* (1989), 244: 1288-1292), and TALENs (described in Sommer et al., Chromosome Research (2015), 23: 43-55, and Cermak et al., *Nucleic Acids Research* (2011): gkr218.).

In one embodiment, gene inactivation is achieved by a CRISPR/Cas system. CRISPR-Cas and similar gene targeting systems are well known in the art with reagents and protocols readily available. Exemplary genome editing protocols are described in Jennifer Doudna, and Prashant Mali, "CRISPR-Cas: A Laboratory Manual" (2016) (CSHL Press, ISBN: 978-1-621821-30-4) and Ran, F. Ann, et al. *Nature Protocols* (2013), 8 (11): 2281-2308.

In some embodiments, the genetically-modified bacterium is selected from the group consisting of *P. aeruginosa, P. alcaligenes, P. anguilliseptica, P. argentinensis, P. borborid, P. citronellolis, P. flavescens, P. mendocina, P. nitroreducens, P. oleovorans, P. pseudoalcaligenes, P. resinovorans, P. straminea, P. asplenii, P. aurantiaca, P. aureofaciens, P. chlororaphis, P. corrugate, P. fragi, P. lundensis, P. taetrolens, P. antarctica, P. azotoformans, P. blatchfordae, P. brassicacearum, P. brenneri, P. cedrina, P. corrugate, P. fluorescens, P. gessardii, P. libanensis, P. mandelii, P. marginalis, P. mediterranea, P. meridiana, P. migulae, P. mucidolens, P. orientalis, P. panacis, P. protegens, P. proteolytica, P. rhodesiae, P. synxantha, P. thivervalensis, P. tolaasii, P. veronii, P. denitrificans, P. pertucinogena, P. putida group, P. cremoricolorata, P. entomophila, P. fulva, P. monteilii, P. mosselii, P. oryzihabitans, P. parafulva, P. plecoglossicida, P. putida, P. balearica, P. luteola, P. stutzeri, P. amygdali, P. avellanae, P. caricapapayae, P. cichorii, P. coronafaciens, P. ficuserectae, P. helianthin, P. meliae, P. savastanoi, P. syringae, P. tomato, P. viridiflava, P. abietaniphila, P. acidophila, P. agarici, P. alcaliphila, P. alkanolytica, P. amyloderamosa, P. asplenii, P. azotifigens, P. cannabina, P. coenobios, P. congelans, P. costantinii, P. cruciviae, P. delhiensis, P. excibis, P. extremorientalis, P. frederiksbergensis, P. fuscovaginae, P. gelidicola, P. grimontii, P. indica, P. jessenii, P. jinjuensis, P. kilonensis, P. knackmussii, P. koreensis, P. lini, P. lutea, P. moraviensis, P. otitidis, P. pachastrellae, P. palleroniana, P. papaveris, P. peli, P. perolens, P. poae, P. pohangensis, P. protegens, P. psychrophile, P. psychrotolerans, P. rathonis, P. reptilivora, P. resiniphila, P. rhizosphaerae, P. rubescens, P. salomonii, P. segitis, P. septica, P. simiae, P. suis, P. teessidea, P. thermotolerans, P. toyotomiensis, P. tremae, P. trivialis, P. turbinellae, P. tuticorinensis, P. umsongensis, P. vancouverensis, P. vranovensis, P. xanthomarina*, and *P. taiwanensis*. In a specific embodiment, the bacterium is of the species *P. putida*.

Methods for Converting an Organic Compound to Mcl-Alcohols

Another aspect of the disclosure is directed to a method for converting an organic compound to a medium chain length alcohol, the method comprising inoculating a medium comprising said organic compound with a genetically-modified bacterium disclosed herein.

In some embodiments, the organic compound is a carbon source. In some embodiments, the carbon source is lignin, or a breakdown product of lignin (e.g., p-coumaric acid, ferulic acid, and saccharides). In some embodiments, the organic compound is selected from aromatic compounds, saccharides, organic acids, and alcohols. In some embodiments, the organic compound is a saccharide, not limited to a saccharide that *Pseudomonas* species can natively consume (e.g., glucose) but also one that the *Pseudomonas* species have been engineered to consume (e.g., xylose and arabinose). In some embodiments, the organic compound is an aromatic compound, and the aromatic compound comprises coumarate, ferulate, or benzoate. In some embodiments, the organic compound is an organic acid, and the organic compound comprises diacids (e.g., succinic acid), or fatty acids (e.g., acetic acid and octanoic acid). In some embodiments, the organic compound is a waste product from the production of biodiesel. In a specific embodiment, the waste product from the production of biodiesel is glycerol.

In some embodiments, the growth of the bacterium is limited due to limited quantities of an essential nutrient in the medium, and the medium comprises sufficient carbon from a carbon source. As used herein, a "limited quantity of an essential nutrient" refers to an amount of an essential nutrient in a media, wherein the ratio of amount of carbon to amount of the essential nutrient ratio (the carbon to essential nutrient ratio) is 3:1 or greater. In some embodiments, the carbon to essential nutrient ratio of the medium is 3:1, 4:1, 5:1, 6:1, 12.5:2, 25:4, 7:1, 8:1, 9:1, 10:1 or higher. Without being limited to a particular theory, it is believed that limiting the amount of an essential nutrient (e.g., nitrogen, phosphorus or sulfur) relative to the amount of carbon (i.e., if the carbon: nutrient ratio is greater than 3:1) diverts carbon into the storage polymer PHAs. The inventors take advantage of this to drive carbon flux to our products of interest like mcl-alcohols. By knocking out the PHA biosynthetic genes, the inventors can maintain the natural carbon flux through fatty acid biosynthesis but convert the intermediates into the alcohols rather than PHAs. In addition, limiting an essential nutrient limits the amount of carbon lost to biomass accumulation (increase in the biomass of the bacterium) by diverting the carbon to production of PHAs. In some embodiments, the essential nutrient which is in limited quantity is nitrogen. In some embodiments, a non-limiting growth medium comprises 25 mM carbon and 12.5 mM nitrogen (a 2:1 carbon:nitrogen ratio). In some embodiments a limiting growth medium comprises 25 mM carbon and 4 mM nitrogen (a 25:4 carbon:nitrogen ratio). In some embodiments a limiting growth medium comprises 12.5 mM carbon and 2 mM nitrogen (a 12.5:2 carbon:nitrogen ratio).

In some embodiments, the method comprises inoculating a medium comprising an organic compound with a genetically-modified bacterium from a *Pseudomonas* species at an initial concentration of at least $10^3$ cfu/ml, at least $10^4$ cfu/ml, at least $10^5$ cfu/ml, at least $10^6$ cfu/ml, at least $10^7$ cfu/ml, at least $10^8$ cfu/ml, at least $10^9$ cfu/ml, or at least $10^{10}$ cfu/ml.

In some embodiments, the mcl-alcohol production is achieved when the genetically-modified bacterium is in a log phase of growth, and thus the genetically modified bacterium can be cultured until at least after the bacterium has entered into a log phase of growth. In some embodiments, mcl-alcohol production is achieved when the genetically-modified bacterium is in a stationary phase of growth, and thus the genetically modified bacterium can be cultured until at least after the bacterium has entered a stationary phase of growth.

In some embodiments, the method comprises growing the genetically modified bacterium under aerobic conditions during mcl-alcohol production.

In some embodiments, the method comprises growing the genetically modified bacterium at about 30° C. In some embodiments, the method comprises growing the genetically modified bacterium at about 25° C., about 27° C., about 29° C., about 30° C., about 31° C., about 33° C., or about 35° C.

In some embodiments, the mcl-alcohol produced contains between 8-16 carbons. In some embodiments, the mcl-alcohol is an octanol (an alcohol with 8 carbons—C8). In some embodiments, the mcl-alcohol is a decanol (an alcohol with 10 carbons—C10). In some embodiments, the mcl-alcohol is a dodecanol (an alcohol with twelve carbons—C12). In some embodiments, the mcl-alcohol is a tetradecanol (an alcohol with 14 carbons—C14). In some embodiments, the mcl-alcohol is a hexadecanol (an alcohol with 16 carbons—C16). In some embodiments, the mcl-alcohol is a mixture of mcl-alcohols that comprise between 8-16 carbons.

In some embodiments, the methods of the disclosure result in mcl-alcohol titers of at least 20 mg/L, at least 25 mg/L, at least 30 mg/L, at least 35 mg/L, at least 40 mg/L, at least 45 mg/L, at least 50 mg/L, at least 55 mg/L, at least 60 mg/L, at least 100 mg/L or higher. In a specific embodiment, the methods result in an mcl-alcohol titer of at least 37.6 mg/L.

In some embodiments, the produced mcl-alcohol is further purified. In some embodiments, the produced mcl-alcohol is purified using phase separation. In some embodiments, the mcl-alcohol is phase separated from the aqueous bacterial culture into an organic solvent layer. In some embodiments, the organic solvent is hexane. In some embodiments, the organic solvent is dodecane. In some embodiments, the phase separation is done during the culturing process as the hexane is an overlay and continuously separates the mcl-alcohols. In some embodiments, the organic layer is separated from the aqueous layer by freezing the mixture to further drive phase separation and allow for easier removal. In some embodiments, the organic layer is sampled for quantification of mcl-alcohols.

Unless defined otherwise, all technical and scientific terms used herein have the same meaning as commonly understood by one skilled in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The present disclosure is further illustrated by the following non-limiting examples.

EXAMPLES

Example 1: Making Engineered *Pseudomonas* Strains

The inventors of the present disclosure have engineered a genetically engineered bacterium that can produce medium chain alcohols (mcl-alcohols). The genetically engineered bacterium is superior in that it can produce high value products from discarded carbon sources, such as waste lignin streams, and thereby improve the sustainability of production.

*Pseudomonas putida* can naturally catabolize many aromatic monomers that are generated in the lignin depolymerization process. The carbon from these monomers is funneled into central carbon metabolism as acetyl-CoA and succinate. When cultured in conditions of carbon excess and limited nitrogen, *P. putida* natively redirects carbon flux through fatty acid biosynthesis to fatty hydroxy-acyl-CoA intermediates, which can be polymerized into poly-hydroxyalkanoates (PHA) for carbon storage. This natural shift in carbon flux provides a platform for two-stage bioprocesses where biocatalyst growth can be controlled to improve product yields.

By deleting the endogenous poly-hydroxyalkanoates synthase genes phaC1 and phaC2, the inventors disrupted the polymerization of PHAs and allowed for the hydroxy-acyl-CoA intermediates to be directed to the alcohol production pathway. To further inhibit the loss of intermediates, several fatty acid degradation genes were deleted. Specifically, the genes fadBA, fadAxBxEx, fadE, and qedHI/II were deleted to decrease competition with the alcohol production pathway. The complete deletion of these genes established a platform strain that was utilized to evaluate the heterologous expression of mcl-alcohol producing enzymes.

Following the deletion of these genes, the inventors introduced production pathways to the bacteria wherein an enoyl-CoA reductase (ter from *Euglena gracilis* and fabI from *Escherichia coli*) was expressed in combination with an acyl-CoA reductase (*Marinobacter aquaeolei* VT8 acr2 gene; Maqu2507). The enoyl-CoA reductase catalyzes the reduction of trans-2-enoyl-CoA intermediates generated from the hydroxy-acyl-CoA intermediate. The acyl-CoA reductase then completes the terminal reduction of the fatty acyl-CoA to the medium chain length alcohols (FIG. 1).

Example 2: Testing the Genetically-Engineered Bacteria

Figure 2:
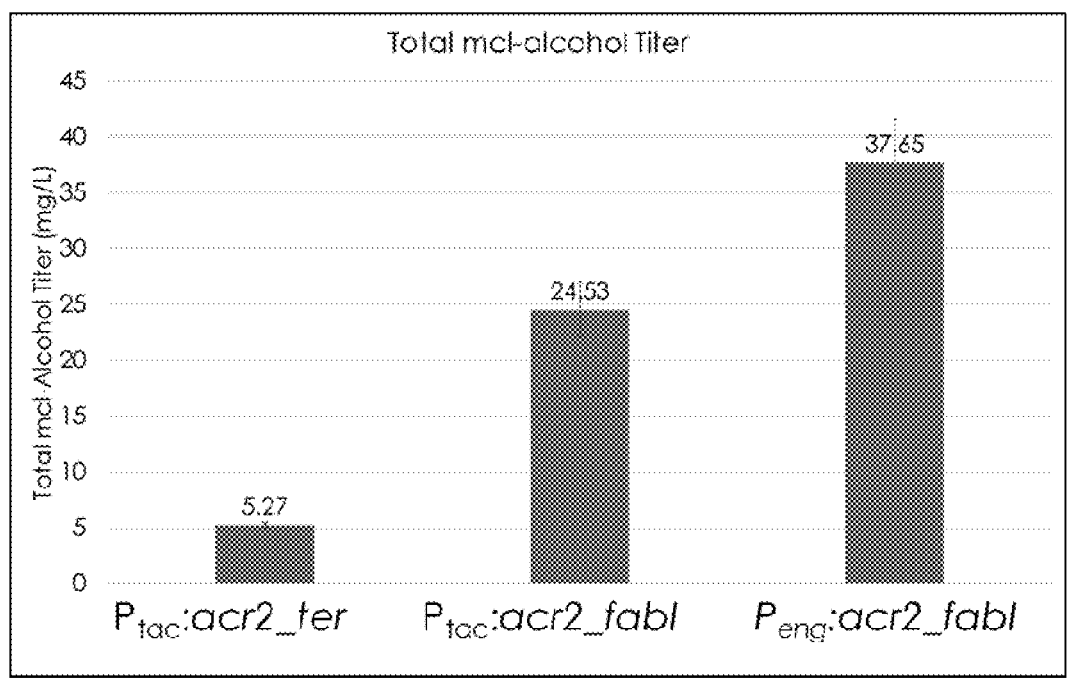
FIG. 2. Total mcl-Alcohol Titer. Titers generated from production strains having heterologous expression of acyl-CoA reductase (acr2) with either trans-enoyl reductase (ter) or fabI. Expression is driven via the tac promoter or engineered promoters.

Initial pathway evaluation was carried out using the σ70 based tac promoter, which produced total mcl-alcohol up to titers of approximately 25 mg/L (FIG. 2). This represents the first demonstration of mcl-alcohol production from lignin derived substrates.

The tac promoter is not expressed well in the nitrogen limited conditions used for mcl-alcohol production, so the inventors evaluated mcl-alcohol production pathway expression with several engineered promoters that express in both growth phase and N-limitation conditions. The best performing engineered promoter was able to increase total mcl-alcohol titers by more than 50%, to a titer of 37.6 mg/L (FIG. 2).

Example 3: Carbon/Nitrogen Ratio Affects Alcohol Production Yield

To further investigate the production capacity of the engineered strains, the inventors evaluated multiple culturing conditions. Established methods to produce mcl-PHAs in *P. putida* utilized p-coumaric acid as the carbon source and $NH_4$ as the nitrogen source in an M9 minimal media. These compounds are usually set at concentrations of 12.5 mM p-coumaric acid and 2 mM $NH_4$.

Figure 3A:
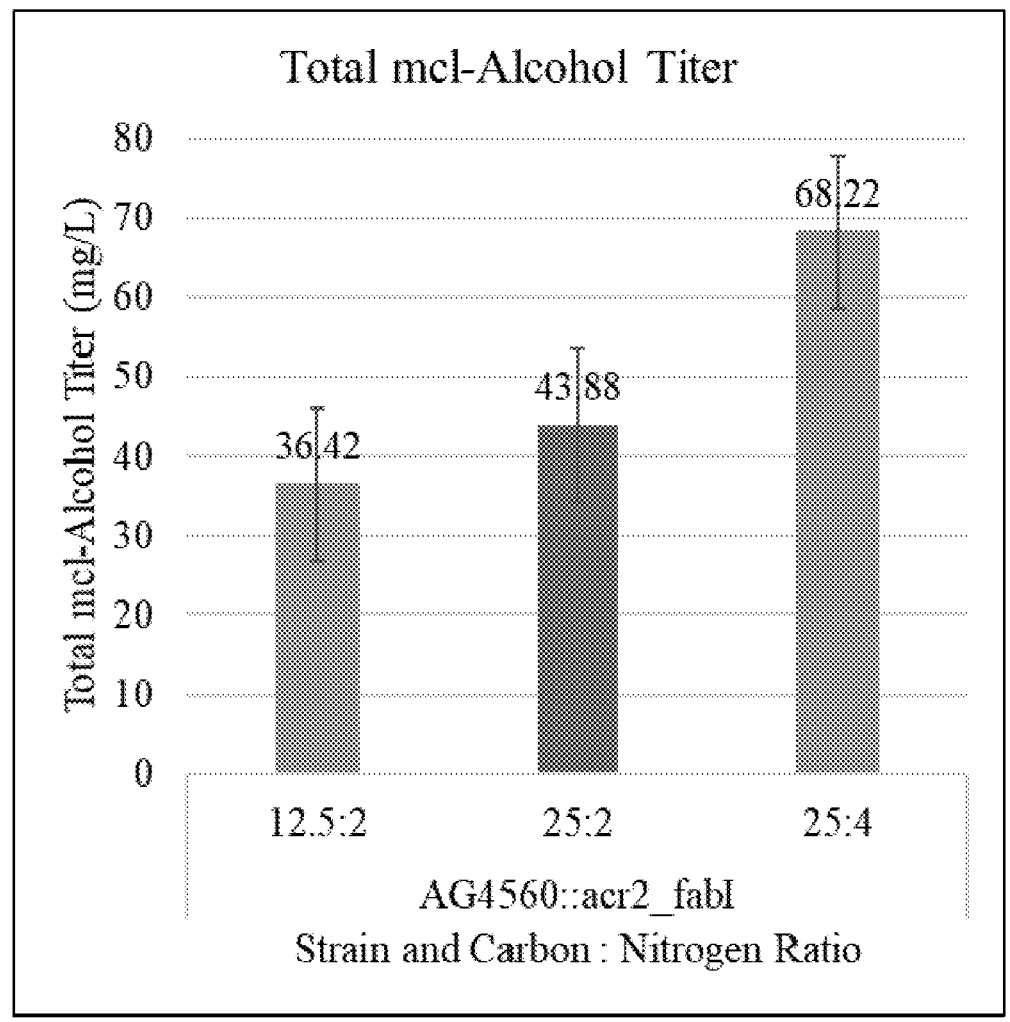
FIGS. 3A-3B. Carbon Loading. Production strain AG4560 was evaluated under different carbon loadings and carbon to nitrogen ratios. (A) Production of mcl-alchohol different carbon loadings and carbon to nitrogen ratios. (B) Percent consumption of the carbon source p-coumarate. Doubling of carbon and nitrogen concentrations resulted in a near doubling of mcl-alcohol production with near complete consumption of carbon. Doubling of carbon but not nitrogen resulted in an increase of 20% total mcl-alcohol titer with incomplete consumption of carbon.
Figure 3B:
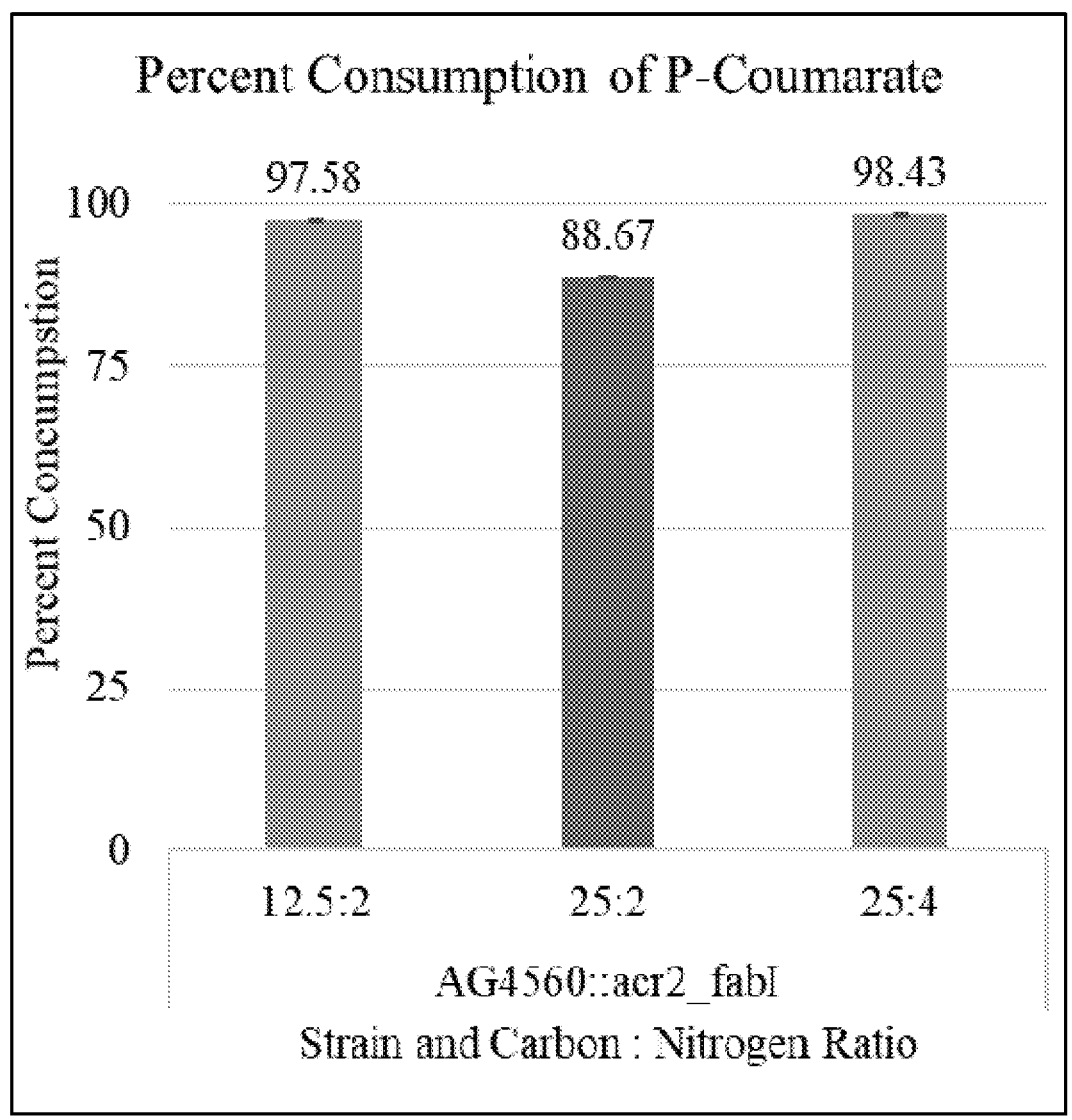

The inventors altered these conditions to double the concentrations of both carbon and nitrogen along with conditions where only the carbon concentration was doubled. When the carbon concentration alone was doubled, the total mcl-alcohol titer increased by 20% and approximately 12% of the carbon supplied remained in the media after 48 hours. In the double carbon and nitrogen conditions, our strain was able to approximately double the total titer of mcl-alcohols to 68 mg/L and consume nearly all the carbon (FIGS. 3A-3B). This data suggests that the carbon loading can be scaled to higher amounts that would be more industrially relevant, but that the carbon to nitrogen ratio plays an important role in product formation.

In summary, the inventors have generated a strain of *P. putida* that can produce nearly 70 mg/L total mcl-alcohols from a lignin derived aromatic monomer. This provides a platform to produce valuable chemicals from a low-cost carbon source to increase the viability and sustainability of lignocellulosic biomass utilization.

TABLE 1

Sequences of Endogenous Genes from *P. putida* utilized in this disclosure

| Gene Name | Type | SEQ ID NO |
| --- | --- | --- |
| PHA Synthase 1 | Nucleotide | 6 |
| PHA Synthase 1 | Protein | 7 |
| PHA Synthase 2 | Nucleotide | 8 |
| PHA Synthase 2 | Protein | 9 |
| PHA Depolymerase | Nucleotide | 10 |
| PHA Depolymerase | Protein | 11 |
| Transposase PP_2134 | Nucleotide | 12 |
| Transposase PP_2134 | Protein | 13 |
| Enoyl-CoA hydratase/3-Hydroxy-CoA Dehydrogenase | Nucleotide | 14 |
| Enoyl-CoA hydratase/3-Hydroxy-CoA Dehydrogenase | Protein | 15 |
| Beta-ketoadipyl-CoA Thiolase | Nucleotide | 16 |
| Beta-ketoadipyl-CoA Thiolase | Protein | 17 |
| Hydroxy acyl-CoA dehydrogenase | Nucleotide | 18 |
| Hydroxy acyl-CoA dehydrogenase | Protein | 19 |
| Acetyl-CoA acetyltransferase | Nucleotide | 20 |
| Acetyl-CoA acetyltransferase | Protein | 21 |
| Acyl-CoA Dehydrogenase | Nucleotide | 22 |
| Acyl-CoA Dehydrogenase | Protein | 23 |
| Enoyl-CoA Hydratase | Nucleotide | 24 |
| Enoyl-CoA Hydratase | Protein | 25 |
| Transposase PP_2218 | Nucleotide | 26 |
| Transposase PP_2218 | Protein | 27 |
| Hypothetical Protein | Nucleotide | 28 |
| Hypothetical Protein | Protein | 29 |
| Medium-long chain acyl-CoA dehydrogenase (fadE) | Nucleotide | 30 |
| Medium-long chain acyl-CoA dehydrogenase (fadE) | Protein | 31 |
| PQQ alcohol dehydrogenase 1 | Nucleotide | 32 |
| PQQ alcohol dehydrogenase 1 | Protein | 33 |
| PQQ alcohol dehydrogenase 2 | Nucleotide | 34 |
| PQQ alcohol dehydrogenase 2 | Protein | 35 |

TABLE 2

Sequences of gene homology regions used to target endogenous *P. putida* genes.

| Targeted Gene | Region | SEQ ID NO |
| --- | --- | --- |
| Transposase PP_2134 | Upstream | 36 |
| Transposase PP_2134 | Downstream | 37 |
| PQQ alcohol dehydrogenase 1 | Upstream | 38 |
| PQQ alcohol dehydrogenase 1 | Downstream | 39 |
| PQQ alcohol dehydrogenase 2 | Upstream | 40 |
| PQQ alcohol dehydrogenase 2 | Downstream | 41 |
| Hydroxy acyl-CoA dehydrogenase | Upstream | 42 |
| Hydroxy acyl-CoA dehydrogenase | Downstream | 43 |
| PHA Synthase 1 | Upstream | 44 |
| PHA Synthase 1 | Downstream | 45 |

What is claimed is:

1. A genetically-modified bacterium from the genus *Pseudomonas*, comprising an exogenous nucleic acid encoding an enoyl-CoA reductase comprising the amino acid sequence as shown in SEQ ID NO: 1 and an exogenous nucleic acid encoding an acyl-CoA reductase comprising the amino acid sequence as shown in SEQ ID NO: 3, wherein the endogenous phaC1 and phaC2 genes that encode polyhydroxyalkanoates (PHA) synthases are mutated to be inactivated in the bacterium and the genetically-modified bacterium produces at least 25 mg/L medium chain length alcohol when inoculated in a medium comprising an organic compound.

2. The genetically-modified bacterium of claim 1, wherein the exogenous nucleic acid encoding an enoyl-CoA reductase is codon optimized for the species of the genus *Pseudomonas* to which the genetically modified bacterium belongs.

3. The genetically-modified bacterium of claim 1, wherein the exogenous nucleic acid encoding an acyl-CoA reductase is codon optimized for the species of the genus *Pseudomonas* to which the genetically modified bacterium belongs.

4. The genetically-modified bacterium of claim 1, wherein the endogenous genes that encode PQQ-dependent alcohol dehydrogenase enzymes are mutated to be inactivated in the bacterium.

5. The genetically-modified bacterium of claim 1, wherein the exogenous nucleic acid encoding an enoyl-CoA reductase and the exogenous nucleic acid encoding an acyl-CoA reductase are placed in the same vector.

6. The genetically-modified bacterium of claim 1, wherein the exogenous nucleic acid encoding an enoyl-CoA reductase and the exogenous nucleic acid encoding an acyl-CoA reductase are placed in separate vectors.

7. The genetically-modified bacterium of claim 1, wherein the bacterium is selected from the group consisting of *P. aeruginosa, P. alcaligenes, P. anguilliseptica, P. argentinensis, P. borborid, P. citronellolis, P. flavescens, P. mendocina, P. nitroreducens, P. oleovorans, P. pseudoalcaligenes, P. resinovorans, P. straminea, P. asplenii, P. aurantiaca, P. aureofaciens, P. chlororaphis, P. corrugate, P. fragi, P. lundensis, P. taetrolens, P. antarctica, P. azotoformans, P. blatchfordae, P. brassicacearum, P. brenneri, P. cedrina, P. corrugate, P. fluorescens, P. gessardii, P. libanensis, P. mandelii, P. marginalis, P. mediterranea, P. meridiana, P. migulae, P. mucidolens, P. orientalis, P. panacis, P. protegens, P. proteolytica, P. rhodesiae, P. synxantha, P. thivervalensis, P. tolaasii, P. veronii, P. denitrificans, P. pertucinogena, P. putida* group, *P. cremoricolorata, P. entomophila, P. fulva, P. monteilii, P. mosselii, P. oryzihabitans, P. parafulva, P. plecoglossicida, P. putida, P. balearica, P. luteola, P. stutzeri, P. amygdali, P. avellanae, P. caricapapayae, P. cichorii, P. coronafaciens, P. ficuserectae, P. helianthin, P. meliae, P. savastanoi, P. syringae, P. tomato, P. viridiflava, P. abietaniphila, P. acidophila, P. agarici, P. alcaliphila, P. alkanolytica, P. amyloderamosa, P. asplenii, P. azotifigens, P. cannabina, P. coenobios, P. congelans, P. costantinii, P. cruciviae, P. delhiensis, P. excibis, P. extremorientalis, P. frederiksbergensis, P. fuscovaginae, P. gelidi-* cola, *P. grimontii, P. indica, P. jessenii, P. jinjuensis, P. kilonensis, P. knackmussii, P. koreensis, P. lini, P. lutea, P. moraviensis, P. otitidis, P. pachastrellae, P. palleroniana, P. papaveris, P. peli, P. perolens, P. poae, P. pohangensis, P. protegens, P. psychrophile, P. psychrotolerans, P. rathonis, P. reptilivora, P. resiniphila, P. rhizosphaerae, P. rubescens, P. salomonii, P. segitis, P. septica, P. simiae, P. suis, P. teessidea, P. thermotolerans, P. toyotomiensis, P. tremae, P. trivialis, P. turbinellae, P. tuticorinensis, P. umsongensis, P. vancouverensis, P. vranovensis, P. xanthomarina*, and *P. taiwanensis*.

8. A method for converting an organic compound to a medium chain length alcohol, the method comprising inoculating a medium comprising said organic compound with the genetically-modified bacterium of claim 1, thereby converting said organic compound to a medium chain length alcohol.

9. The method of claim 8, wherein the enoyl-CoA reductase encoded by the exogenous nucleic acid is an enzyme from a bacterium that is not *Pseudomonas*.

10. The method of claim 9, wherein the enoyl-CoA reductase is an enzyme from a bacterial species that belongs to the genus *Escherichia*.

11. The method of claim 8, wherein the exogenous nucleic acid encoding an enoyl-CoA reductase is codon optimized for the species of the genus *Pseudomonas* to which the genetically modified bacterium belongs.

12. The method of claim 8, wherein the acyl-CoA reductase is an enzyme from a proteobacterial species that belongs to the genus *Marinobacter*.

13. The method of claim 8, wherein the exogenous nucleic acid encoding an acyl-CoA reductase is codon optimized for the species of the genus *Pseudomonas* to which the genetically modified bacterium belongs.

14. The method of claim 8, wherein the endogenous genes that encode polyhydroxyalkanoates (PHA) synthases are mutated to be inactivated in the bacterium.

15. The method of claim 8, wherein the endogenous genes that encode PQQ-dependent alcohol dehydrogenase enzymes are mutated to be inactivated in the bacterium.

16. The method of claim 8, wherein the organic compound comprises a carbon source.

17. The method of claim 16, wherein the carbon source comprises a breakdown product of lignin.

18. The method of claim 17, wherein the breakdown product of lignin comprises p-coumaric acid, ferulic acid, or saccharides.

19. The method of claim 8, wherein the medium comprises a limited quantity of an essential nutrient.

20. The method of claim 19, wherein the essential nutrient is nitrogen.

21. The method of claim 20, wherein the ratio of the amount of the carbon to the amount of the nitrogen in the media is about 25:4.

22. The method of claim 8, wherein the exogenous nucleic acid encoding an enoyl-CoA reductase and the exogenous nucleic acid encoding an acyl-CoA reductase are placed in the same vector.

23. The method of claim 8, wherein the exogenous nucleic acid encoding an enoyl-CoA reductase and the exogenous nucleic acid encoding an acyl-CoA reductase are placed in separate vectors.

24. The method of claim 8, wherein the bacterium is selected from the group consisting of *P. aeruginosa, P. alcahgenes, P. anguilliseptica, P. argentinensis, P. borborid, P. citronellolis, P. flavescens, P. mendocina, P. nitroreducens, P. oleovorans, P. pseudoalcaligenes, P. resinovorans, P. straminea, P. asplenii, P. aurantiaca, P. aureofaciens, P. chlororaphis, P. corrugate, P. fragi, P. lundensis, P. taetrolens, P. antarctica, P. azotoformans, P. blatchfordae, P. brassicacearum, P. brenneri, P. cedrina, P. corrugate, P. fluorescens, P. gessardii, P. libanensis, P. mandelii, P. marginalis, P. mediterranea, P. meridiana, P. migulae, P. mucidolens, P. orientalis, P. panacis, P. protegens, P. proteolytica, P. rhodesiae, P. synxantha, P. thivervalensis, P. tolaasii, P. veronii, P. denitrificans, P. pertucinogena, P. putida* group, *P. cremoricolorata, P. entomophila, P. fulva, P. monteilii, P. mosselii, P. oryzihabitans, P. parafulva, P. plecoglossicida, P. putida, P. balearica, P. luteola, P. stutzeri, P. amygdali, P. avellanae, P. caricapapayae, P. cichorii, P. coronafaciens, P. ficuserectae, P. helianthin, P. meliae, P. savastanoi, P. syringae, P. tomato, P. viridiflava, P. abietaniphila, P. acidophila, P. agarici, P. alcaliphila, P. alkanolytica, P. amyloderamosa, P. asplenii, P. azotifigens, P. cannabina, P. coenobios, P. congelans, P. costantinii, P. cruciviae, P. delhiensis, P. excibis, P. extremorientalis, P. frederiksbergensis, P. fuscovaginae, P. gelidicola, P. grimontii, P. indica, P. jessenii, P. jinjuensis, P. kilonensis, P. knackmussii, P. koreensis, P. lini, P. lutea, P. moraviensis, P. otitidis, P. pachastrellae, P. palleroniana, P. papaveris, P. peli, P. perolens, P. poae, P. pohangensis, P. protegens, P. psychrophile, P. psychrotolerans, P. rathonis, P. reptilivora, P. resiniphila, P. rhizosphaerae, P. rubescens, P. salomonii, P. segitis, P. septica, P. simiae, P. suis, P. teessidea, P. thermotolerans, P. toyotomiensis, P. tremae, P. trivialis, P. turbinellae, P. tuticorinensis, P. umsongensis, P. vancouverensis, P. vranovensis, P. xanthomarina*, and *P. taiwanensis*.

* * * * *

SEQUENCE LISTING

<160> NUMBER OF SEQ ID NOS: 45

<210> SEQ ID NO 1

<211> LENGTH: 262
<212> TYPE: PRT
<213> ORGANISM: Escherichia coli

<400> SEQUENCE: 1

```
Met Gly Phe Leu Ser Gly Lys Arg Ile Leu Val Thr Gly Val Ala Ser
1               5                   10                  15
Lys Leu Ser Ile Ala Tyr Gly Ile Ala Gln Ala Met His Arg Glu Gly
                20                  25                  30
Ala Glu Leu Ala Phe Thr Tyr Gln Asn Asp Lys Leu Lys Gly Arg Val
            35                  40                  45
Glu Glu Phe Ala Ala Gln Leu Gly Ser Asp Ile Val Leu Gln Cys Asp
        50                  55                  60
Val Ala Glu Asp Ala Ser Ile Asp Thr Met Phe Ala Glu Leu Gly Lys
65                  70                  75                  80
Val Trp Pro Lys Phe Asp Gly Phe Val His Ser Ile Gly Phe Ala Pro
                85                  90                  95
Gly Asp Gln Leu Asp Gly Asp Tyr Val Asn Ala Val Thr Arg Glu Gly
                100                 105                 110
Phe Lys Ile Ala His Asp Ile Ser Ser Tyr Ser Phe Val Ala Met Ala
            115                 120                 125
Lys Ala Cys Arg Ser Met Leu Asn Pro Gly Ser Ala Leu Leu Thr Leu
        130                 135                 140
Ser Tyr Leu Gly Ala Glu Arg Ala Ile Pro Asn Tyr Asn Val Met Gly
145                 150                 155                 160
Leu Ala Lys Ala Ser Leu Glu Ala Asn Val Arg Tyr Met Ala Asn Ala
                165                 170                 175
Met Gly Pro Glu Gly Val Arg Val Asn Ala Ile Ser Ala Gly Pro Ile
                180                 185                 190
Arg Thr Leu Ala Ala Ser Gly Ile Lys Asp Phe Arg Lys Met Leu Ala
            195                 200                 205
His Cys Glu Ala Val Thr Pro Ile Arg Arg Thr Val Thr Ile Glu Asp
        210                 215                 220
Val Gly Asn Ser Ala Ala Phe Leu Cys Ser Asp Leu Ser Ala Gly Ile
225                 230                 235                 240
Ser Gly Glu Val Val His Val Asp Gly Gly Phe Ser Ile Ala Ala Met
                245                 250                 255
Asn Glu Leu Glu Leu Lys
            260
```

<210> SEQ ID NO 2
<211> LENGTH: 789
<212> TYPE: DNA
<213> ORGANISM: Escherichia coli

<400> SEQUENCE: 2

```
atgggcttct tgagcggcaa acgcattctg gtgaccggcg tggcctcgaa actgtcgatt      60
gcgtatggca tcgcccaggc catgcaccgc gaaggcgcgg aactggcctt cacctaccag     120
aacgacaaac tgaagggccg ggtggaggag tttgccgcgc agctgggcag cgacattgtg     180
ctgcaatgcg acgtggcgga ggacgcctcg atcgatacca tgttcgcgga gctgggtaag     240
gtctggccga agttcgacgg cttcgtccac agcatcggct cgcccgggg cgatcagctg      300
gacggggact acgtcaatgc cgtgacccgc gagggcttta agatcgccca cgatatcagc     360
tcctacagct tgtcgcgat ggccaaagcc tgtcgcagca tgctgaaccc gggcagcgcc      420
```

-continued

```
ctgctgacgc tgagctacct gggcgccgag cgggccatcc cgaattacaa cgtcatgggc    480
ttggccaaag cgagcttgga ggccaacgtc cgctatatgg ccaatgcgat gggcccggaa    540
ggcgtgcggg tcaacgccat cagcgcgggc ccgatccgca ccctggcggc gtccggtatc    600
aaagacttcc gcaagatgtt ggcgcactgc gaggccgtga ccccgatccg ccgcaccgtc    660
accatcgaag atgtgggcaa cagcgcggcg ttcttgtgca gcgacctgag cgccggcatt    720
tcgggcgagg tggtgcatgt ggatggtggg ttcagcatcg ccgccatgaa cgagctggag    780
ctgaagtga                                                           789
```

<210> SEQ ID NO 3
<211> LENGTH: 661
<212> TYPE: PRT
<213> ORGANISM: Artificial Sequence
<220> FEATURE:
<223> OTHER INFORMATION: Marinobacter aquaeolei

<400> SEQUENCE: 3

```
Met Asn Tyr Phe Leu Thr Gly Gly Thr Gly Phe Ile Gly Arg Phe Leu
1               5                   10                  15

Val Glu Lys Leu Leu Ala Arg Gly Gly Thr Val Tyr Val Leu Val Arg
            20                  25                  30

Glu Gln Ser Gln Asp Lys Leu Glu Arg Leu Arg Glu Arg Trp Gly Ala
        35                  40                  45

Asp Asp Lys Gln Val Lys Ala Val Ile Gly Asp Leu Thr Ser Lys Asn
    50                  55                  60

Leu Gly Ile Asp Ala Lys Thr Leu Lys Ser Leu Lys Gly Asn Ile Asp
65                  70                  75                  80

His Val Phe His Leu Ala Ala Val Tyr Asp Met Gly Ala Asp Glu Glu
                85                  90                  95

Ala Gln Ala Ala Thr Asn Ile Glu Gly Thr Arg Ala Ala Val Gln Ala
            100                 105                 110

Ala Glu Ala Met Gly Ala Lys His Phe His Val Ser Ser Ile Ala
            115                 120                 125

Ala Ala Gly Leu Phe Lys Gly Ile Phe Arg Glu Asp Met Phe Glu Glu
        130                 135                 140

Ala Glu Lys Leu Asp His Pro Tyr Leu Arg Thr Lys His Glu Ser Glu
145                 150                 155                 160

Lys Val Val Arg Glu Glu Cys Lys Val Pro Phe Arg Ile Tyr Arg Pro
                165                 170                 175

Gly Met Val Ile Gly His Ser Glu Thr Gly Glu Met Asp Lys Val Asp
            180                 185                 190

Gly Pro Tyr Tyr Phe Phe Lys Met Ile Gln Lys Ile Arg His Ala Leu
        195                 200                 205

Pro Gln Trp Val Pro Thr Ile Gly Ile Glu Gly Arg Leu Asn Ile
    210                 215                 220

Val Pro Val Asp Phe Val Val Asp Ala Leu Asp His Ile Ala His Leu
225                 230                 235                 240

Glu Gly Glu Asp Gly Asn Cys Phe His Leu Val Asp Ser Asp Pro Tyr
                245                 250                 255

Lys Val Gly Glu Ile Leu Asn Ile Phe Cys Glu Ala Gly His Ala Pro
            260                 265                 270

Arg Met Gly Met Arg Ile Asp Ser Arg Met Phe Gly Phe Ile Pro Pro
        275                 280                 285

Phe Ile Arg Gln Ser Ile Lys Asn Leu Pro Pro Val Lys Arg Ile Thr
```

```
            290                 295                 300
Gly Ala Leu Leu Asp Asp Met Gly Ile Pro Pro Ser Val Met Ser Phe
305                 310                 315                 320

Ile Asn Tyr Pro Thr Arg Phe Asp Thr Arg Glu Leu Glu Arg Val Leu
                325                 330                 335

Lys Gly Thr Asp Ile Glu Val Pro Arg Leu Pro Ser Tyr Ala Pro Val
            340                 345                 350

Ile Trp Asp Tyr Trp Glu Arg Asn Leu Asp Pro Asp Leu Phe Lys Asp
        355                 360                 365

Arg Thr Leu Lys Gly Thr Val Glu Gly Lys Val Cys Val Val Thr Gly
370                 375                 380

Ala Thr Ser Gly Ile Gly Leu Ala Thr Ala Glu Lys Leu Ala Glu Ala
385                 390                 395                 400

Gly Ala Ile Leu Val Ile Gly Ala Arg Thr Lys Glu Thr Leu Asp Glu
                405                 410                 415

Val Ala Ala Ser Leu Glu Ala Lys Gly Gly Asn Val His Ala Tyr Gln
            420                 425                 430

Cys Asp Phe Ser Asp Met Asp Asp Cys Asp Arg Phe Val Lys Thr Val
        435                 440                 445

Leu Asp Asn His Gly His Val Asp Val Leu Val Asn Asn Ala Gly Arg
450                 455                 460

Ser Ile Arg Arg Ser Leu Ala Leu Ser Phe Asp Arg Phe His Asp Phe
465                 470                 475                 480

Glu Arg Thr Met Gln Leu Asn Tyr Phe Gly Ser Val Arg Leu Ile Met
                485                 490                 495

Gly Phe Ala Pro Ala Met Leu Glu Arg Arg Gly His Val Val Asn
            500                 505                 510

Ile Ser Ser Ile Gly Val Leu Thr Asn Ala Pro Arg Phe Ser Ala Tyr
        515                 520                 525

Val Ser Ser Lys Ser Ala Leu Asp Ala Phe Ser Arg Cys Ala Ala Ala
530                 535                 540

Glu Trp Ser Asp Arg Asn Val Thr Phe Thr Thr Ile Asn Met Pro Leu
545                 550                 555                 560

Val Lys Thr Pro Met Ile Ala Pro Thr Lys Ile Tyr Asp Ser Val Pro
                565                 570                 575

Thr Leu Thr Pro Asp Glu Ala Ala Gln Met Val Ala Asp Ala Ile Val
            580                 585                 590

Tyr Arg Pro Lys Arg Ile Ala Thr Arg Leu Gly Val Phe Ala Gln Val
        595                 600                 605

Leu His Ala Leu Ala Pro Lys Met Gly Glu Ile Ile Met Asn Thr Gly
610                 615                 620

Tyr Arg Met Phe Pro Asp Ser Pro Ala Ala Gly Ser Lys Ser Gly
625                 630                 635                 640

Glu Lys Pro Lys Val Ser Thr Glu Gln Val Ala Phe Ala Ala Ile Met
                645                 650                 655

Arg Gly Ile Tyr Trp
            660

<210> SEQ ID NO 4
<211> LENGTH: 1986
<212> TYPE: DNA
<213> ORGANISM: Artificial Sequence
<220> FEATURE:
<223> OTHER INFORMATION: Marinobacter aquaeolei
```

<400> SEQUENCE: 4

```
atgaactatt ttctgacggg cggtaccggg ttcattggcc gcttcctggt ggagaagctg    60
ctggcccggg gcggcacggt ctacgtgctg gtgcgcgaac agagccagga caagttggag   120
cgcctgcgcg agcggtgggg ggccgacgat aaacaggtga aggccgtgat cggtgacctg   180
acctcgaaaa acctgggcat tgacgccaag accctgaagt cgctgaaggg caacatcgac   240
catgtgtttc acctggccgc cgtgtacgac atgggcgccg acgaggaggc gcaggcggcg   300
accaacatcg aaggtacccg tgccgccgtc caggccgccg aagcgatggg cgccaaacat   360
ttccatcatg tgagctcgat tgccgccgcc ggtttgttca agggtatctt ccgcgaggac   420
atgtttgagg aggcggaaaa gctggatcac ccgtacctgc gcaccaaaca cgaaagcgaa   480
aaggtggtgc gtgaagagtg caaggtcccc tttcgcatct accgtccggg catggtgatt   540
ggccacagcg aaaccggcga aatggataaa gtggatggcc cgtactactt tttcaagatg   600
atccagaaaa tccgccacgc gctgccacag tgggtcccga ccatcggcat cgaaggcggc   660
cggctgaaca ttgtcccggt ggatttcgtc gtggacgccc tggaccatat tgcccacctg   720
gagggcgagg atggcaactg cttccacttg gtggacagcg atccatacaa ggtcggtgag   780
atcttgaaca tcttctgcga agccggccac gcgccacgga tgggcatgcg cattgacagc   840
cgcatgttcg gcttcatccc gcccttcatc cgtcagagca tcaagaacct gcccccccgtg  900
aagcgcatca ccggcgccct tgctggacgac atgggcatcc cgccctccgt gatgagcttc   960
attaactacc ccacccgctt cgatacccgc gaactggaac gcgtcctgaa gggtaccgac  1020
atcgaagtgc cccgcctgcc aagctacgcg ccagtgatct gggactactg gaacggaat   1080
ctggacccgg acctgttcaa ggatcgcacc ctgaagggca ccgtcgaggg gaaggtgtgc  1140
gtcgtgaccg gcgccacgtc gggcatcggg ctggcgaccg ccgagaagtt ggccgaagcg  1200
ggcgcgatcc tggtgattgg cgcgcgcacg aaagaaacct ggacgaagt cgccgcgagc  1260
ctggaagcga agggcggcaa cgtgcacgcc taccagtgcg actttagcga tatgatgac   1320
tgcgatcgct tcgtcaaaac cgtcttggac aaccacggcc acgtggacgt gctggtgaac  1380
aacgccggtc gctcgatccg gcgcagcctg gcgttgagct tcgaccgctt ccacgacttc  1440
gagcgcacga tgcagctgaa ctacttcggt agcgtgcgtc tgatcatggg gttcgcgccg  1500
gccatgctgg aacgtcgccg ggggcacgtc gtgaacatct cctcgatcgg cgtcctgacc  1560
aacgccccc gcttcagcgc ctacgtgtcg tccaaaagcg cgttggatgc gttctcgcgc  1620
tgtgccgccg ccgaatggag cgaccgcaac gtgaccttca cgacgatcaa catgccactg  1680
gtgaaaaccc cgatgattgc cccgacgaag atctatgact ccgtgcccac cctgaccccg  1740
gatgaagcgg cccagatggt cgcggacgcc atcgtgtacc gcccgaagcg gattgcgacc  1800
cgcttgggcg tgttcgcgca ggtcttgcac gcgctggccc caagatgggc cgagattatc  1860
atgaacaccg ctaccgcat gttcccggat agcccggccg cggcgggcag caaaagcggc  1920
gaaaagccca aggtgagcac ggaacaggtc gcgttcgccg ccattatgcg cggcatttac  1980
tggtga                                                             1986
```

<210> SEQ ID NO 5
<211> LENGTH: 539
<212> TYPE: PRT
<213> ORGANISM: Euglena gracilis

<400> SEQUENCE: 5

Met Ser Cys Pro Ala Ser Pro Ser Ala Ala Val Val Ser Ala Gly Ala

-continued

```
1               5                   10                  15
Leu Cys Leu Cys Val Ala Thr Val Leu Leu Ala Thr Gly Ser Asn Pro
                20                  25                  30

Thr Ala Leu Ser Thr Ala Ser Thr Arg Ser Pro Thr Ser Leu Val Arg
                35                  40                  45

Gly Val Asp Arg Gly Leu Met Arg Pro Thr Thr Ala Ala Leu Thr
                50                  55                  60

Thr Met Arg Glu Val Pro Gln Met Ala Glu Gly Phe Ser Gly Glu Ala
65                  70                  75                  80

Thr Ser Ala Trp Ala Ala Gly Pro Gln Trp Ala Ala Pro Leu Val
                85                  90                  95

Ala Ala Ala Ser Ser Ala Leu Ala Leu Trp Trp Ala Ala Arg Arg
                100                 105                 110

Ser Val Arg Arg Pro Leu Ala Ala Leu Ala Glu Leu Pro Thr Ala Val
                115                 120                 125

Thr His Leu Ala Pro Pro Met Ala Met Phe Thr Thr Thr Ala Lys Val
                130                 135                 140

Ile Gln Pro Lys Ile Arg Gly Phe Ile Cys Thr Thr His Pro Ile
145                 150                 155                 160

Gly Cys Glu Lys Arg Val Gln Glu Glu Ile Ala Tyr Ala Arg Ala His
                165                 170                 175

Pro Pro Thr Ser Pro Gly Pro Lys Arg Val Leu Val Ile Gly Cys Ser
                180                 185                 190

Thr Gly Tyr Gly Leu Ser Thr Arg Ile Thr Ala Ala Phe Gly Tyr Gln
                195                 200                 205

Ala Ala Thr Leu Gly Val Phe Leu Ala Gly Pro Pro Thr Lys Gly Arg
                210                 215                 220

Pro Ala Ala Ala Gly Trp Tyr Asn Thr Val Ala Phe Glu Lys Ala Ala
225                 230                 235                 240

Leu Glu Ala Gly Leu Tyr Ala Arg Ser Leu Asn Gly Asp Ala Phe Asp
                245                 250                 255

Ser Thr Thr Lys Ala Arg Thr Val Glu Ala Ile Lys Arg Asp Leu Gly
                260                 265                 270

Thr Val Asp Leu Val Val Tyr Ser Ile Ala Ala Pro Lys Arg Thr Asp
                275                 280                 285

Pro Ala Thr Gly Val Leu His Lys Ala Cys Leu Lys Pro Ile Gly Ala
                290                 295                 300

Thr Tyr Thr Asn Arg Thr Val Asn Thr Asp Lys Ala Glu Val Thr Asp
305                 310                 315                 320

Val Ser Ile Glu Pro Ala Ser Pro Glu Glu Ile Ala Asp Thr Val Lys
                325                 330                 335

Val Met Gly Gly Glu Asp Trp Glu Leu Trp Ile Gln Ala Leu Ser Glu
                340                 345                 350

Ala Gly Val Leu Ala Glu Gly Ala Lys Thr Val Ala Tyr Ser Tyr Ile
                355                 360                 365

Gly Pro Glu Met Thr Trp Pro Val Tyr Trp Ser Gly Thr Ile Gly Glu
                370                 375                 380

Ala Lys Lys Asp Val Glu Lys Ala Lys Arg Ile Thr Gln Gln Tyr
385                 390                 395                 400

Gly Cys Pro Ala Tyr Pro Val Val Ala Lys Ala Leu Val Thr Gln Ala
                405                 410                 415

Ser Ser Ala Ile Pro Val Val Pro Leu Tyr Ile Cys Leu Leu Tyr Arg
                420                 425                 430
```

```
Val Met Lys Glu Lys Gly Thr His Glu Gly Cys Ile Glu Gln Met Val
        435                 440                 445
Arg Leu Leu Thr Thr Lys Leu Tyr Pro Glu Asn Gly Ala Pro Ile Val
    450                 455                 460
Asp Glu Ala Gly Arg Val Arg Val Asp Asp Trp Glu Met Ala Glu Asp
465                 470                 475                 480
Val Gln Gln Ala Val Lys Asp Leu Trp Ser Gln Val Ser Thr Ala Asn
                485                 490                 495
Leu Lys Asp Ile Ser Asp Phe Ala Gly Tyr Gln Thr Glu Phe Leu Arg
                500                 505                 510
Leu Phe Gly Phe Gly Ile Asp Gly Val Asp Tyr Asp Gln Pro Val Asp
            515                 520                 525
Val Glu Ala Asp Leu Pro Ser Ala Ala Gln Gln
    530                 535
```

<210> SEQ ID NO 6
<211> LENGTH: 1680
<212> TYPE: DNA
<213> ORGANISM: Pseudomonas putida

<400> SEQUENCE: 6

```
atgagtaaca agaacaacga tgagctacag cggcaggcct cggaaaacac cctggggctg      60
aacccggtca tcggcatccg ccgcaaggac ctgttgagct cggcacgcac cgtgctgcgc     120
caggccgtgc gccaaccgct gcacagcgcc aagcatgtgg ctcactttgg cctggagctg     180
aagaacgtgt tgctgggcaa atccagcctg gccccggaca cgacgaccg tcgcttcaat     240
gacccggcct ggagcaacaa cccgctgtac cgccgctacc tgcaaaccta cctggcctgg     300
cgcaaggagc tgcaggactg ggtgagcagc agcgacctgt cccccagga catcagccgc     360
ggccagttcg tcatcaacct gatgaccgag gccatggcgc cgaccaatac cctgtccaac     420
ccggctgcgg tcaaacgctt cttcgaaacc ggcggcaaga gcctgctcga tggcctgtcc     480
aacctggcca aggacatggt caacaacggc ggcatgccca gccaggtgaa catggatgcc     540
ttcgaagtgg gcaagaacct gggcaccagc gaaggcgcgg tggtgtaccg caacgatgtg     600
ctggaactga tccagtacag ccccatcacc gagcaggtgc atgcccgtcc gctgctggtg     660
gtgccaccgc agatcaacaa gttctacgtg ttcgacctca gcccggaaaa gagcctggcg     720
cgcttctgcc tgcgctcgca gcagcagacc ttcatcatca gctggcgcaa cccgaccaag     780
gcccagcgtg aatggggcct gtccacctac atcgatgcgc tgaaagaagc cgtcgacgcg     840
gtgctgtcga ttaccggcag caaggacctg aacatgctcg gcgcctgctc cggtggcatc     900
acttgtaccg cactggtggg ccactatgcc gccattggcg agaacaaggt caacgccctg     960
accctgctgg tcagcgtgct ggacaccacc atggacaacc aggttgcttt gtttgtcgac    1020
gagcagacct ggaggccgc caagcgccac tcctatcagg cgggcgtgct ggaaggcagc    1080
gaaatggcca aggtgttcgc ctggatgcgc cccaacgacc tgatctggaa ctactgggta    1140
aacaactacc tgctcggcaa tgagccccccg tgttcgaca tcctgttctg aacaacgac    1200
accacgcgcc tgccggccgc cttccacgga gacctgatcg aaatgttcaa gagcaacccg    1260
ctgacccgcc ccgacgccct ggaagtgtgc ggcaccgcga tcgacctgaa acaggtcaaa    1320
tgcgacatct acagcctcgc cggcaccaac gaccacatca cccctggcc gtcatgctac    1380
cgctcggcac atctgttcgg cggcaagatc gaattcgtac tgtccaacag cgggcatatc    1440
cagagcatcc tcaacccgcc gggcaacccg aaggcacgtt tcatgaccgg tgccgatcgc    1500
```

```
ccgggtgacc cggtggcctg gcaggaaaat gccatcaagc atgcagactc ctggtggttg     1560
cactggcaga gttggctggg cgagcgtgcc ggcgcgctga aaaaggcacc gacccgcctg     1620
ggcaaccgta cctatgccgc cggcgaagcc tccccaggca cctacgttca cgagcgttga     1680
```

<210> SEQ ID NO 7
<211> LENGTH: 559
<212> TYPE: PRT
<213> ORGANISM: Pseudomonas putida

<400> SEQUENCE: 7

```
Met Ser Asn Lys Asn Asn Asp Glu Leu Gln Arg Gln Ala Ser Glu Asn
1               5                   10                  15

Thr Leu Gly Leu Asn Pro Val Ile Gly Ile Arg Arg Lys Asp Leu Leu
            20                  25                  30

Ser Ser Ala Arg Thr Val Leu Arg Gln Ala Val Arg Gln Pro Leu His
        35                  40                  45

Ser Ala Lys His Val Ala His Phe Gly Leu Glu Leu Lys Asn Val Leu
    50                  55                  60

Leu Gly Lys Ser Ser Leu Ala Pro Asp Ser Asp Asp Arg Arg Phe Asn
65                  70                  75                  80

Asp Pro Ala Trp Ser Asn Asn Pro Leu Tyr Arg Arg Tyr Leu Gln Thr
                85                  90                  95

Tyr Leu Ala Trp Arg Lys Glu Leu Gln Asp Trp Val Ser Ser Ser Asp
            100                 105                 110

Leu Ser Pro Gln Asp Ile Ser Arg Gly Gln Phe Val Ile Asn Leu Met
        115                 120                 125

Thr Glu Ala Met Ala Pro Thr Asn Thr Leu Ser Asn Pro Ala Ala Val
    130                 135                 140

Lys Arg Phe Phe Glu Thr Gly Gly Lys Ser Leu Leu Asp Gly Leu Ser
145                 150                 155                 160

Asn Leu Ala Lys Asp Met Val Asn Gly Gly Met Pro Ser Gln Val
                165                 170                 175

Asn Met Asp Ala Phe Glu Val Gly Lys Asn Leu Gly Thr Ser Glu Gly
            180                 185                 190

Ala Val Val Tyr Arg Asn Asp Val Leu Glu Leu Ile Gln Tyr Ser Pro
        195                 200                 205

Ile Thr Glu Gln Val His Ala Arg Pro Leu Leu Val Val Pro Pro Gln
    210                 215                 220

Ile Asn Lys Phe Tyr Val Phe Asp Leu Ser Pro Glu Lys Ser Leu Ala
225                 230                 235                 240

Arg Phe Cys Leu Arg Ser Gln Gln Gln Thr Phe Ile Ile Ser Trp Arg
                245                 250                 255

Asn Pro Thr Lys Ala Gln Arg Glu Trp Gly Leu Ser Thr Tyr Ile Asp
            260                 265                 270

Ala Leu Lys Glu Ala Val Asp Ala Val Leu Ser Ile Thr Gly Ser Lys
        275                 280                 285

Asp Leu Asn Met Leu Gly Ala Cys Ser Gly Gly Ile Thr Cys Thr Ala
    290                 295                 300

Leu Val Gly His Tyr Ala Ala Ile Gly Glu Asn Lys Val Asn Ala Leu
305                 310                 315                 320

Thr Leu Leu Val Ser Val Leu Asp Thr Thr Met Asp Asn Gln Val Ala
                325                 330                 335

Leu Phe Val Asp Glu Gln Thr Leu Glu Ala Ala Lys Arg His Ser Tyr
```

```
                340               345               350
Gln Ala Gly Val Leu Glu Gly Ser Glu Met Ala Lys Val Phe Ala Trp
        355               360               365
Met Arg Pro Asn Asp Leu Ile Trp Asn Tyr Trp Val Asn Asn Tyr Leu
    370               375               380
Leu Gly Asn Glu Pro Pro Val Phe Asp Ile Leu Phe Trp Asn Asn Asp
385               390               395               400
Thr Thr Arg Leu Pro Ala Ala Phe His Gly Asp Leu Ile Glu Met Phe
                405               410               415
Lys Ser Asn Pro Leu Thr Arg Pro Asp Ala Leu Glu Val Cys Gly Thr
            420               425               430
Ala Ile Asp Leu Lys Gln Val Lys Cys Asp Ile Tyr Ser Leu Ala Gly
        435               440               445
Thr Asn Asp His Ile Thr Pro Trp Pro Ser Cys Tyr Arg Ser Ala His
    450               455               460
Leu Phe Gly Gly Lys Ile Glu Phe Val Leu Ser Asn Ser Gly His Ile
465               470               475               480
Gln Ser Ile Leu Asn Pro Pro Gly Asn Pro Lys Ala Arg Phe Met Thr
                485               490               495
Gly Ala Asp Arg Pro Gly Asp Pro Val Ala Trp Gln Glu Asn Ala Ile
            500               505               510
Lys His Ala Asp Ser Trp Trp Leu His Trp Gln Ser Trp Leu Gly Glu
        515               520               525
Arg Ala Gly Ala Leu Lys Lys Ala Pro Thr Arg Leu Gly Asn Arg Thr
    530               535               540
Tyr Ala Ala Gly Glu Ala Ser Pro Gly Thr Tyr Val His Glu Arg
545               550               555
```

<210> SEQ ID NO 8
<211> LENGTH: 1683
<212> TYPE: DNA
<213> ORGANISM: Pseudomonas putida

<400> SEQUENCE: 8

```
atgacagaca aaccggccaa aggatcgaca acgctccccg ccacccgcat gaacgtgcag      60
aacgccatcc tcggcctgcg cggccgcgac ctgctttcca cgctgcgcaa cgtcggccgc     120
cacggcctgc gccacccgct gcataccgcg catcatctgc tggcgcttgg cgggcagttg     180
gggcgggtga tgctggggga cacgccctac cagccgaacc gcgtgacgc acgcttcagt     240
gaccccgacct ggagccagaa cccgttctac cgccgcggcc tgcaagccta tctggcctgg     300
cagaagcaga cacgccagtg gatcgatgaa agccatttga cgacgatga tcgagcccgc     360
gcccacttcc tgttcaacct gatcaacgat gcgctggcgc ccagcaactc actgctcaat     420
ccgttggcgg tcaaggagct gttcaacacc ggcggccaga gcctggtgcg cggcgtggct     480
cacctgctcg acgacctgcg tcacaacgat gggctgcctc gtcaggtgga cgagcgcgcc     540
ttcgaagtgg gcgttaacct ggccgcaacc cctggcgcag tggtatttcg caacgagctg     600
ctggagctga tccagtactc gccgatgagc gaaaagcagc acgcacgccc actgctggtc     660
gtgccgcctc agatcaacaa gttctacatc ttcgacctca gcgcgaccaa cagcttcgtc     720
cagtacatgc tcaaaagcgg cttgcaggtg ttcatggtca gctggcgcaa ccccgaccca     780
cgccaccgtg aatggggcct ttccagctat gtgcaagccc tggaggaagc gctcaatgcc     840
tgccgcagta tcagcggcaa ccgcgacccc aacctgatgg gtgcctgtgc cggcggcctg     900
```

```
accatggccg cactgcaagg ccatctgcaa gccaagaagc aattgcgccg ggtgcgcagt    960
gccacgtatc tggtcagctt gctggacagc aagttcgaaa gcccggccag cctgttcgcc   1020
gatgagcaga ccatcgaagc ggccaagcga cgctcctatc agcgtggcgt gctggacggt   1080
ggtgaagtgg cgcggatctt cgcctggatg cggcccaacg acctgatctg gaactactgg   1140
gtaaacaact acctgctcgg caagacaccg ccggcgttcg acatcctgta ctggaatgcc   1200
gacagcacgc gcctgcccgc cgcgctgcat ggcgacctgc tggagttttt caagctcaac   1260
cccttgacct acgcgtccgg gctggaggtg tgcggtacgc cgatcgacct gcagcaggtc   1320
aatatcgaca gctttaccgt ggccggcagc aacgaccaca tcacaccatg ggatgcggtg   1380
taccgctcgg ccttgctgct gggtggcgag cggcgcttcg tgctggccaa cagcgggcat   1440
atccagagca tcatcaaccc gccaggcaac cccaaggcct actacctggc caaccccaag   1500
ctgagcagcg acccacgcgc ctggttccac gacgccaagc gcagtgaagg cagctggtgg   1560
ccgttgtggc tggagtggat caccgcacgc tccggcctgc tcaaggcacc gcgtactgaa   1620
ctgggcaacg ccacttaccc accgctaggc cccgcgccag caacctacgt gctgacccga   1680
tga                                                                 1683
```

<210> SEQ ID NO 9
<211> LENGTH: 560
<212> TYPE: PRT
<213> ORGANISM: Pseudomonas putida

<400> SEQUENCE: 9

```
Met Thr Asp Lys Pro Ala Lys Gly Ser Thr Thr Leu Pro Ala Thr Arg
1               5                   10                  15

Met Asn Val Gln Asn Ala Ile Leu Gly Leu Arg Gly Arg Asp Leu Leu
            20                  25                  30

Ser Thr Leu Arg Asn Val Gly Arg His Gly Leu Arg His Pro Leu His
        35                  40                  45

Thr Ala His His Leu Leu Ala Leu Gly Gly Gln Leu Gly Arg Val Met
    50                  55                  60

Leu Gly Asp Thr Pro Tyr Gln Pro Asn Pro Arg Asp Ala Arg Phe Ser
65                  70                  75                  80

Asp Pro Thr Trp Ser Gln Asn Pro Phe Tyr Arg Arg Gly Leu Gln Ala
                85                  90                  95

Tyr Leu Ala Trp Gln Lys Gln Thr Arg Gln Trp Ile Asp Glu Ser His
            100                 105                 110

Leu Asn Asp Asp Arg Ala Arg Ala His Phe Leu Phe Asn Leu Ile
        115                 120                 125

Asn Asp Ala Leu Ala Pro Ser Asn Ser Leu Leu Asn Pro Leu Ala Val
    130                 135                 140

Lys Glu Leu Phe Asn Thr Gly Gly Gln Ser Leu Val Arg Gly Val Ala
145                 150                 155                 160

His Leu Leu Asp Asp Leu Arg His Asn Asp Gly Leu Pro Arg Gln Val
                165                 170                 175

Asp Glu Arg Ala Phe Glu Val Gly Val Asn Leu Ala Ala Thr Pro Gly
            180                 185                 190

Ala Val Val Phe Arg Asn Glu Leu Leu Glu Leu Ile Gln Tyr Ser Pro
        195                 200                 205

Met Ser Glu Lys Gln His Ala Arg Pro Leu Leu Val Val Pro Pro Gln
    210                 215                 220

Ile Asn Lys Phe Tyr Ile Phe Asp Leu Ser Ala Thr Asn Ser Phe Val
```

```
            225                 230                 235                 240
    Gln Tyr Met Leu Lys Ser Gly Leu Gln Val Phe Met Val Ser Trp Arg
                        245                 250                 255

Asn Pro Asp Pro Arg His Arg Glu Trp Gly Leu Ser Ser Tyr Val Gln
                        260                 265                 270

Ala Leu Glu Glu Ala Leu Asn Ala Cys Arg Ser Ile Ser Gly Asn Arg
                        275                 280                 285

Asp Pro Asn Leu Met Gly Ala Cys Ala Gly Gly Leu Thr Met Ala Ala
                        290                 295                 300

Leu Gln Gly His Leu Gln Ala Lys Lys Gln Leu Arg Arg Val Arg Ser
    305                 310                 315                 320

Ala Thr Tyr Leu Val Ser Leu Leu Asp Ser Lys Phe Glu Ser Pro Ala
                        325                 330                 335

Ser Leu Phe Ala Asp Glu Gln Thr Ile Glu Ala Ala Lys Arg Arg Ser
                        340                 345                 350

Tyr Gln Arg Gly Val Leu Asp Gly Gly Glu Val Ala Arg Ile Phe Ala
                        355                 360                 365

Trp Met Arg Pro Asn Asp Leu Ile Trp Asn Tyr Trp Val Asn Asn Tyr
    370                 375                 380

Leu Leu Gly Lys Thr Pro Pro Ala Phe Asp Ile Leu Tyr Trp Asn Ala
    385                 390                 395                 400

Asp Ser Thr Arg Leu Pro Ala Ala Leu His Gly Asp Leu Leu Glu Phe
                        405                 410                 415

Phe Lys Leu Asn Pro Leu Thr Tyr Ala Ser Gly Leu Glu Val Cys Gly
                        420                 425                 430

Thr Pro Ile Asp Leu Gln Gln Val Asn Ile Asp Ser Phe Thr Val Ala
                        435                 440                 445

Gly Ser Asn Asp His Ile Thr Pro Trp Asp Ala Val Tyr Arg Ser Ala
                        450                 455                 460

Leu Leu Leu Gly Gly Glu Arg Arg Phe Val Leu Ala Asn Ser Gly His
    465                 470                 475                 480

Ile Gln Ser Ile Ile Asn Pro Pro Gly Asn Pro Lys Ala Tyr Tyr Leu
                        485                 490                 495

Ala Asn Pro Lys Leu Ser Ser Asp Pro Arg Ala Trp Phe His Asp Ala
                        500                 505                 510

Lys Arg Ser Glu Gly Ser Trp Trp Pro Leu Trp Leu Glu Trp Ile Thr
                        515                 520                 525

Ala Arg Ser Gly Leu Leu Lys Ala Pro Arg Thr Glu Leu Gly Asn Ala
                        530                 535                 540

Thr Tyr Pro Pro Leu Gly Pro Ala Pro Gly Thr Tyr Val Leu Thr Arg
    545                 550                 555                 560

<210> SEQ ID NO 10
<211> LENGTH: 852
<212> TYPE: DNA
<213> ORGANISM: Pseudomonas putida

<400> SEQUENCE: 10
atgccgcaac cctatatttt caggaccgtc gagctggaca accagtccat ccgcaccgct      60
gttcgccccg gcaagccgca cctgacgccg ttgctgatct ttaacggcat cggcgccaac     120
ctcgagctgg tgttcccgtt catcgatgca cttgacccgg acctggaagt catcgccttt     180
gatgtgcccg gggtcggcgg ctcgtctacg ccacgcaacc cgtaccgctt ccctgggctg     240
gccaagctga ccgcgcggat gctcgactac ctcgactacg ccaggtcaa cgtcatcggc     300
```

```
gtgtcctggg gcggcgccct ggcccagcag tttgctcacg attacccga gcgctgcaag    360 aagctggtgc tggccgccac cgctgccggt cggtaatgg tgccaggcaa gcccaaggtg    420
ctgtggatga tggccagccc ccggcgttac gtgcagccat cgcatgtcat ccgcattgcg    480
ccgatgatct atggcggcgg cttccgacgt gaccccgacc tggccatgca ccatgccgcc    540
aaggtgcgct ccggcggcaa gctgggctac tactggcagc tgttcgcagg gctcggctgg    600
accagcatcc actggctgca caagatccgg cagcccaccc tggtactggc tggcgacgac    660
gacccgttga tcccgctgat caacatgcgc ctgctggcct ggcggattcc caatgcccag    720
ctacacatta tcgacgacgg ccatctgttc ctgatcaccc gtgccgaagc cgtcgccccg    780
atcatcatga agttcctgca ggaagaacgt cagcgtgcgg tcatgcatcc ccgtccggcc    840
tcgggggggt ga                                                       852
```

<210> SEQ ID NO 11
<211> LENGTH: 283
<212> TYPE: PRT
<213> ORGANISM: Pseudomonas putida

<400> SEQUENCE: 11

```
Met Pro Gln Pro Tyr Ile Phe Arg Thr Val Glu Leu Asp Asn Gln Ser
1               5                   10                  15

Ile Arg Thr Ala Val Arg Pro Gly Lys Pro His Leu Thr Pro Leu Leu
            20                  25                  30

Ile Phe Asn Gly Ile Gly Ala Asn Leu Glu Leu Val Phe Pro Phe Ile
        35                  40                  45

Asp Ala Leu Asp Pro Asp Leu Glu Val Ile Ala Phe Asp Val Pro Gly
    50                  55                  60

Val Gly Gly Ser Ser Thr Pro Arg Asn Pro Tyr Arg Phe Pro Gly Leu
65                  70                  75                  80

Ala Lys Leu Thr Ala Arg Met Leu Asp Tyr Leu Asp Tyr Gly Gln Val
                85                  90                  95

Asn Val Ile Gly Val Ser Trp Gly Gly Ala Leu Ala Gln Gln Phe Ala
            100                 105                 110

His Asp Tyr Pro Glu Arg Cys Lys Lys Leu Val Leu Ala Ala Thr Ala
        115                 120                 125

Ala Gly Ala Val Met Val Pro Gly Lys Pro Lys Val Leu Trp Met Met
    130                 135                 140

Ala Ser Pro Arg Arg Tyr Val Gln Pro Ser His Val Ile Arg Ile Ala
145                 150                 155                 160

Pro Met Ile Tyr Gly Gly Gly Phe Arg Arg Asp Pro Asp Leu Ala Met
                165                 170                 175

His His Ala Ala Lys Val Arg Ser Gly Gly Lys Leu Gly Tyr Tyr Trp
            180                 185                 190

Gln Leu Phe Ala Gly Leu Gly Trp Thr Ser Ile His Trp Leu His Lys
        195                 200                 205

Ile Arg Gln Pro Thr Leu Val Leu Ala Gly Asp Asp Pro Leu Ile
    210                 215                 220

Pro Leu Ile Asn Met Arg Leu Leu Ala Trp Arg Ile Pro Asn Ala Gln
225                 230                 235                 240

Leu His Ile Ile Asp Asp Gly His Leu Phe Leu Ile Thr Arg Ala Glu
                245                 250                 255

Ala Val Ala Pro Ile Ile Met Lys Phe Leu Gln Glu Glu Arg Gln Arg
            260                 265                 270
```

Ala Val Met His Pro Arg Pro Ala Ser Gly Gly
            275                 280

<210> SEQ ID NO 12
<211> LENGTH: 966
<212> TYPE: DNA
<213> ORGANISM: Pseudomonas putida

<400> SEQUENCE: 12

```
atggcaatgt ccgcaatccc aatcgaagct ggcgtggaca cctccaaaga tgaactggtg      60
attcaagccg ctccgaatac caaatccttc gccatcccta acactccgaa agcaatcaaa     120
gcctggctca agacgctgcc caaaggctca gcgctggcca tcgaagcgac cagtacctat     180
cacatggaaa tggcggagca agcccatgct gcgggcttcg cggtatacgt tatcgatggg     240
ctgaggctga gtaagtaccg ggaaagtgtt gctatacggg caaaaacaga tgcccatgat     300
gccgctttgc tcgcccgctt cctgagcaac gagcggggct cttttgaagg cttggactccg    360
ccaccagccg gcatcgtga  gatccaggtg ctgctgcgcc gccgccgcaa acttgtagca     420
gtgcgcggca tgctgcggat gagcttgtcg ggcgacaaat tgtttgcctc agaactcaaa     480
cgtgttgagg aagtgctcga acgcatagag ctttcgctgg aaaaacagct gcgtgcggtg     540
atcaagaagg cggggctttc cgatcagatg cgccgtgttc agaggcttcc gggtgttggt     600
ttcttaacgg ctgccggcct ggtgatgtcc ttcatgcgcg cgagttcaa gaacagcgac      660
gcctttgtcg cttatctagg catggatgta acggtttccc aatccggtaa atgggcaggc     720
agagggaagt tgagcaagcg cggagactcg gaggtccgta gactcctgta caacgcctcg    780
atgagcggca gtcgaaccgc gacctggaag cagtattacg cccatcacca gcccgggg      840
aagaaaacca ctcaagcctt ggtgatcctt gcacgtcgct ggctcggct ggccttcggc      900
ctgatgaggc atcaggccga ctggaagccc gagatatata ccggaggtgc aagccggcc      960
agctga                                                               966
```

<210> SEQ ID NO 13
<211> LENGTH: 321
<212> TYPE: PRT
<213> ORGANISM: Pseudomonas putida

<400> SEQUENCE: 13

Met Ala Met Ser Ala Ile Pro Ile Glu Ala Gly Val Asp Thr Ser Lys
1               5                   10                  15

Asp Glu Leu Val Ile Gln Ala Ala Pro Asn Thr Lys Ser Phe Ala Ile
            20                  25                  30

Pro Asn Thr Pro Lys Ala Ile Lys Ala Trp Leu Lys Thr Leu Pro Lys
        35                  40                  45

Gly Ser Ala Leu Ala Ile Glu Ala Thr Ser Thr Tyr His Met Glu Met
    50                  55                  60

Ala Glu Gln Ala His Ala Ala Gly Phe Ala Val Tyr Val Ile Asp Gly
65                  70                  75                  80

Leu Arg Leu Ser Lys Tyr Arg Glu Ser Val Ala Ile Arg Ala Lys Thr
                85                  90                  95

Asp Ala His Asp Ala Ala Leu Leu Ala Arg Phe Leu Ser Asn Glu Arg
            100                 105                 110

Gly Ser Leu Lys Ala Trp Thr Pro Pro Ala Gly His Arg Glu Ile
        115                 120                 125

Gln Val Leu Leu Arg Arg Arg Ala Lys Leu Val Ala Val Arg Gly Met

```
                130              135              140
Leu Arg Met Ser Leu Ser Gly Asp Lys Leu Phe Ala Ser Glu Leu Lys
145                 150                 155                 160

Arg Val Glu Glu Val Leu Glu Arg Ile Glu Leu Ser Leu Glu Lys Gln
                165                 170                 175

Leu Arg Ala Val Ile Lys Lys Ala Gly Leu Ser Asp Gln Met Arg Arg
            180                 185                 190

Val Gln Arg Leu Pro Gly Val Gly Phe Leu Thr Ala Ala Gly Leu Val
        195                 200                 205

Met Ser Phe Met Arg Gly Glu Phe Lys Asn Ser Asp Ala Phe Val Ala
210                 215                 220

Tyr Leu Gly Met Asp Val Thr Val Ser Gln Ser Gly Lys Trp Ala Gly
225                 230                 235                 240

Arg Gly Lys Leu Ser Lys Arg Gly Asp Ser Glu Val Arg Arg Leu Leu
                245                 250                 255

Tyr Asn Ala Ser Met Ser Gly Ser Arg Thr Ala Thr Trp Lys Gln Tyr
            260                 265                 270

Tyr Ala His His Gln Ala Arg Gly Lys Lys Thr Thr Gln Ala Leu Val
        275                 280                 285

Ile Leu Ala Arg Arg Leu Ala Arg Leu Ala Phe Gly Leu Met Arg His
    290                 295                 300

Gln Ala Asp Trp Lys Pro Glu Ile Tyr Thr Gly Gly Ala Lys Pro Ala
305                 310                 315                 320

Ser

<210> SEQ ID NO 14
<211> LENGTH: 2148
<212> TYPE: DNA
<213> ORGANISM: Pseudomonas putida

<400> SEQUENCE: 14
atgatttacg aaggtaaagc catcacggtt aaggctcttg aaagtggcat cgtcgagctc      60
aagttcgacc tcaagggtga gtccgtcaac aagttcaacc gccttaccct gaacgagctg     120
cgccaggccg tcgatgccat ccgggccgat gcttcggtca agggcgtgat cgtcaggagt     180
ggcaaggacg tgttcatcgt cggcgccgac atcaccgagt cgtcgacaa cttcaagctg     240 cctgaggccg aactggtcgc tggcaacctg gaagccaatc gcatcttcaa cgcgttcgaa     300
gacctcgaag tgccgaccgt tgccgccatc aacggcatcg cgctgggcgg cggcctggaa     360
atgtgcctgg cggccgacta ccgggtcatg tccaccagcg ccaggatcgg cctgccggaa     420
gtcaagctgg gtatctaccc gggctttggc ggtaccgtgc gcctgccgcg cctgatcggc     480
tcggacaacg ccatcgagtg gatcgccgcc ggcaaggaaa accgtgccga agatgccctg     540
aaagtggggg ccgtcgacgc cgtggtcgcc cctgagctgc tgctggccgg tgccctcgac     600
ctgatcaagc gtgccatcag tggcgagctg gactacaagg ccaagcgcca gccgaagctg     660
gaaaagctca agctcaatgc catcgagcag atgatggcct tcgagactgc caagggcttc     720
gtcgctggcc aggccggccc gaactacccg gccccggtcg aagcgatcaa gagcatccag     780
aaagccgcca acttcggtcg cgacaaggcc ctggaagtcg aagccgcagg ctttgccaag     840
ctggccaaga cctctgtcgc cgagagcctg atcggcttgt tcctcaacga tcaggaactc     900
aagcgcaagg ccaaggcgca tgacgagatc gcccacgacg tgaagcaggc cgccgtgctc     960
ggcgccggca tcatgggcgg cggtatcgcc taccagtcgg cggtcaaagg tacgccgatc    1020
```

```
ctgatgaagg acatccgcga ggaagccatt cagctgggtc tgaacgaggc ctccaagttg    1080
cttggcaacc gcgtcgagaa gggccgcctg accccggcca agatggccga ggccctcaac    1140
gccattcgcc cgaccctgtc ctatggcgat tcgccaatg tcgacatcgt cgtcgaggct     1200
gtggtcgaga acccgaaggt caagcaagcg gtactggcgg aagtggaagg ccaggtgaag    1260
gacgatgcga tcctcgcttc caacacctct accatctcca tcaacctgct ggccaaggcg    1320
ctcaagcgcc cggaaaactt cgtcggcatg cacttcttca acccggtgca catgatgccg    1380
ctggttgaag tgatccgtgg cgagaagtcc agtgacgtgg cggtcgccac caccgtggcc    1440
tacgccaaga aaatgggcaa gaacccgatc gtggtcaacg actgcccggg cttttttggtc   1500
```

```
Glu Asp Ala Leu Lys Val Gly Ala Val Asp Ala Val Val Ala Pro Glu
            180                 185                 190
Leu Leu Leu Ala Gly Ala Leu Asp Leu Ile Lys Arg Ala Ile Ser Gly
            195                 200                 205
Glu Leu Asp Tyr Lys Ala Lys Arg Gln Pro Lys Leu Glu Lys Leu Lys
            210                 215                 220
Leu Asn Ala Ile Glu Gln Met Met Ala Phe Glu Thr Ala Lys Gly Phe
225                 230                 235                 240
Val Ala Gly Gln Ala Gly Pro Asn Tyr Pro Ala Pro Val Glu Ala Ile
            245                 250                 255
Lys Ser Ile Gln Lys Ala Ala Asn Phe Gly Arg Asp Lys Ala Leu Glu
            260                 265                 270
Val Glu Ala Ala Gly Phe Ala Lys Leu Ala Lys Thr Ser Val Ala Glu
            275                 280                 285
Ser Leu Ile Gly Leu Phe Leu Asn Asp Gln Glu Leu Lys Arg Lys Ala
            290                 295                 300
Lys Ala His Asp Glu Ile Ala His Asp Val Lys Gln Ala Ala Val Leu
305                 310                 315                 320
Gly Ala Gly Ile Met Gly Gly Ile Ala Tyr Gln Ser Ala Val Lys
            325                 330                 335
Gly Thr Pro Ile Leu Met Lys Asp Ile Arg Glu Glu Ala Ile Gln Leu
            340                 345                 350
Gly Leu Asn Glu Ala Ser Lys Leu Leu Gly Asn Arg Val Glu Lys Gly
            355                 360                 365
Arg Leu Thr Pro Ala Lys Met Ala Glu Ala Leu Asn Ala Ile Arg Pro
            370                 375                 380
Thr Leu Ser Tyr Gly Asp Phe Ala Asn Val Asp Ile Val Val Glu Ala
385                 390                 395                 400
Val Val Glu Asn Pro Lys Val Lys Gln Ala Val Leu Ala Glu Val Glu
            405                 410                 415
Gly Gln Val Lys Asp Asp Ala Ile Leu Ala Ser Asn Thr Ser Thr Ile
            420                 425                 430
Ser Ile Asn Leu Leu Ala Lys Ala Leu Lys Arg Pro Glu Asn Phe Val
            435                 440                 445
Gly Met His Phe Phe Asn Pro Val His Met Met Pro Leu Val Glu Val
450                 455                 460
Ile Arg Gly Glu Lys Ser Ser Asp Val Ala Val Ala Thr Thr Val Ala
465                 470                 475                 480
Tyr Ala Lys Lys Met Gly Lys Asn Pro Ile Val Val Asn Asp Cys Pro
            485                 490                 495
Gly Phe Leu Val Asn Arg Val Leu Phe Pro Tyr Phe Gly Phe Ala
            500                 505                 510
Lys Leu Val Ser Ala Gly Val Asp Phe Val Arg Ile Asp Lys Val Met
            515                 520                 525
Glu Lys Phe Gly Trp Pro Met Gly Pro Ala Tyr Leu Met Asp Val Val
            530                 535                 540
Gly Ile Asp Thr Gly His His Gly Arg Asp Val Met Ala Glu Gly Phe
545                 550                 555                 560
Pro Asp Arg Met Lys Asp Glu Arg Ser Ala Val Asp Ala Leu Tyr
            565                 570                 575
Glu Ala Asn Arg Leu Gly Gln Lys Asn Gly Lys Gly Phe Tyr Ala Tyr
            580                 585                 590
Glu Thr Asp Lys Arg Gly Lys Pro Lys Lys Val Phe Asp Ala Thr Val
```

```
                  595                 600                 605
Leu Asp Val Leu Lys Pro Ile Val Phe Glu Gln Arg Glu Val Thr Asp
        610                 615                 620

Glu Asp Ile Ile Asn Trp Met Met Val Pro Leu Cys Leu Glu Thr Val
625                 630                 635                 640

Arg Cys Leu Glu Asp Gly Ile Val Glu Thr Ala Ala Glu Ala Asp Met
            645                 650                 655

Gly Leu Val Tyr Gly Ile Gly Phe Pro Pro Phe Arg Gly Gly Ala Leu
                660                 665                 670

Arg Tyr Ile Asp Ser Ile Gly Val Ala Glu Phe Val Ala Leu Ala Asp
            675                 680                 685

Gln Tyr Ala Asp Leu Gly Pro Leu Tyr His Pro Thr Ala Lys Leu Arg
        690                 695                 700

Glu Met Ala Lys Asn Gly Gln Arg Phe Phe Asn
705                 710                 715

<210> SEQ ID NO 16
<211> LENGTH: 1176
<212> TYPE: DNA
<213> ORGANISM: Pseudomonas putida

<400> SEQUENCE: 16
atgagcctga atccaagaga cgtggtgatt gtcgacttcg gtcgcacgcc aatgggccgc      60
tccaagggtg gcatgcaccg caacacccgc gccgaagaca tgtcggcgca cctgatcagc     120
aagctgctgg aacgcaacgg caaggtcgac ccgaaagaag tcgaggacgt gatctggggc     180
tgcgtcaacc agaccctgga gcagggctgg aacatcgccc gcatggcttc gctgatgacc     240
ccgatcccgc acacctctgc ggcgcagacc gtcagccgcc tgtgcggctc gtccatgagc     300
gcgctgcaca cggccgccca ggcgatcatg accggtaacg gtgatgtgtt cgtggtcggt     360
ggcgtggagc acatgggcca cgtcagcatg atgcatggcg tagaccccaa ccgcacctg      420 tccttgcatg ccgccaaggc ttccgggatg atgggcctga ctgcagaaat gctcggcaag     480
atgcacggca tcacccgtga gcagcaggac ctgttcggct tgcgttcgca ccagctggcc     540
cacaaggcca cggtcgaagg caagttcaag gacgagatca tcccgatgca gggctacgac     600
gagaacggct tcctgaaggt gttcgatttc gacgaaacca ttcgcccgga accaccctc      660 gaaggcctgg catcgctcaa gcctgcgttc aacccgaaag gcgtacggt cacggccggt      720 acctcgtcgc agatcaccga cggcgcctcg tgcatgatcg tcatgtccgg tcagcgtgcc     780
atggacctcg gtatccagcc attggcggtg atccgttcga tggcagtggc cggtgtcgac     840
ccggcaatca tgggctacgg cccggtgcca tcgacccaga agccctcaa gcgtgcgggc      900 ttgaccatgg ccgatatcga cttcatcgag ctcaacgaag ccttcgctgc gcaggccctg     960
cccgtgctga agacttgaa agtgctcgac aagatggatg agaaggttaa cctgcacggc     1020
ggcgccattg ctttgggcca cccgttcggt tgctccgggg cgcggatttc cggcaccctg     1080
ctcaacgtca tgaagcaaaa tggcggtacg ctgggtgttg cgaccatgtg cgtcggcctg     1140
ggccaaggta tcaccactgt cttcgaacgc gtctga                              1176

<210> SEQ ID NO 17
<211> LENGTH: 391
<212> TYPE: PRT
<213> ORGANISM: Pseudomonas putida

<400> SEQUENCE: 17
```

```
Met Ser Leu Asn Pro Arg Asp Val Val Ile Val Asp Phe Gly Arg Thr
  1               5                  10                  15

Pro Met Gly Arg Ser Lys Gly Gly Met His Arg Asn Thr Arg Ala Glu
                 20                  25                  30

Asp Met Ser Ala His Leu Ile Ser Lys Leu Leu Glu Arg Asn Gly Lys
             35                  40                  45

Val Asp Pro Lys Glu Val Glu Asp Val Ile Trp Gly Cys Val Asn Gln
 50                  55                  60

Thr Leu Glu Gln Gly Trp Asn Ile Ala Arg Met Ala Ser Leu Met Thr
 65                  70                  75                  80

Pro Ile Pro His Thr Ser Ala Ala Gln Thr Val Ser Arg Leu Cys Gly
                 85                  90                  95

Ser Ser Met Ser Ala Leu His Thr Ala Ala Gln Ala Ile Met Thr Gly
             100                 105                 110

Asn Gly Asp Val Phe Val Val Gly Val Glu His Met Gly His Val
             115                 120                 125

Ser Met Met His Gly Val Asp Pro Asn Pro His Leu Ser Leu His Ala
     130                 135                 140

Ala Lys Ala Ser Gly Met Met Gly Leu Thr Ala Glu Met Leu Gly Lys
145                 150                 155                 160

Met His Gly Ile Thr Arg Glu Gln Gln Asp Leu Phe Gly Leu Arg Ser
                 165                 170                 175

His Gln Leu Ala His Lys Ala Thr Val Glu Gly Lys Phe Lys Asp Glu
             180                 185                 190

Ile Ile Pro Met Gln Gly Tyr Asp Glu Asn Gly Phe Leu Lys Val Phe
         195                 200                 205

Asp Phe Asp Glu Thr Ile Arg Pro Glu Thr Thr Leu Glu Gly Leu Ala
     210                 215                 220

Ser Leu Lys Pro Ala Phe Asn Pro Lys Gly Gly Thr Val Thr Ala Gly
225                 230                 235                 240

Thr Ser Ser Gln Ile Thr Asp Gly Ala Ser Cys Met Ile Val Met Ser
                 245                 250                 255

Gly Gln Arg Ala Met Asp Leu Gly Ile Gln Pro Leu Ala Val Ile Arg
             260                 265                 270

Ser Met Ala Val Ala Gly Val Asp Pro Ala Ile Met Gly Tyr Gly Pro
     275                 280                 285

Val Pro Ser Thr Gln Lys Ala Leu Lys Arg Ala Gly Leu Thr Met Ala
     290                 295                 300

Asp Ile Asp Phe Ile Glu Leu Asn Glu Ala Phe Ala Ala Gln Ala Leu
305                 310                 315                 320

Pro Val Leu Lys Asp Leu Lys Val Leu Asp Lys Met Asp Glu Lys Val
                 325                 330                 335

Asn Leu His Gly Gly Ala Ile Ala Leu Gly His Pro Phe Gly Cys Ser
             340                 345                 350

Gly Ala Arg Ile Ser Gly Thr Leu Leu Asn Val Met Lys Gln Asn Gly
     355                 360                 365

Gly Thr Leu Gly Val Ala Thr Met Cys Val Gly Leu Gly Gln Gly Ile
 370                 375                 380

Thr Thr Val Phe Glu Arg Val
385                 390
```

<210> SEQ ID NO 18
<211> LENGTH: 768
<212> TYPE: DNA

<213> ORGANISM: Pseudomonas putida

<400> SEQUENCE: 18

```
atgcacatag ccaataaaca tttcatcgtc agcggcgccg cttccgggct gggtgccgcg    60
actgcacaga tgctggtcga ggctggcgcc aaggtcatgc tggtcgacct caatgcccag   120
gctgtcgaag ccaaggcccg cgaactgggc gacaatgccc gtttcgccgt ggctgatatc   180
agtgacgagc aggcggccca gtcggctgtc gatgcagctg tcagcgcctt tggcagcttg   240
catgggttgg tcaattgtgc cggcatcgtc ggtgccgaga aggtgctggg caagcagggc   300
ccgcatggcc tggccagctt cgccaaggtc atcaacgtca acctgatcgg cagcttcaac   360
ctgttgcgtc tggctgcggc ggccatggcc gaaggggctg ccgatgagag cggcgagcgt   420
ggggtcatca tcaacacggc ctccattgcc gcctatgacg gccagattgg ccaggccgcc   480
tacgccgcct ccaagggtgc cattgccagc ctgaccttgc cggccgcgcg cgaactggca   540
cgcttcggca tccgtgtgat gaccatcgct ccgggtatct ttgaaacccc tatgatggcc   600
ggcatgagcg atgaggtacg tgcttcgctg gctgccggcg tgccgttccc gccccgcttg   660
ggccgcccgc aggaatacgc cgcgctggcc cgccacatca tcgagaacag catgctcaac   720
ggtgaggtca tccgcctcga cggtgcgctg cgcatggctg ccaagtaa              768
```

<210> SEQ ID NO 19
<211> LENGTH: 255
<212> TYPE: PRT
<213> ORGANISM: Pseudomonas putida

<400> SEQUENCE: 19

```
Met His Ile Ala Asn Lys His Phe Ile Val Ser Gly Ala Ala Ser Gly
 1               5                   10                  15

Leu Gly Ala Ala Thr Ala Gln Met Leu Val Glu Ala Gly Ala Lys Val
             20                  25                  30

Met Leu Val Asp Leu Asn Ala Gln Ala Val Glu Ala Lys Ala Arg Glu
         35                  40                  45

Leu Gly Asp Asn Ala Arg Phe Ala Val Ala Asp Ile Ser Asp Glu Gln
     50                  55                  60

Ala Ala Gln Ser Ala Val Asp Ala Ala Val Ser Ala Phe Gly Ser Leu
 65                  70                  75                  80

His Gly Leu Val Asn Cys Ala Gly Ile Val Gly Ala Glu Lys Val Leu
                 85                  90                  95

Gly Lys Gln Gly Pro His Gly Leu Ala Ser Phe Ala Lys Val Ile Asn
            100                 105                 110

Val Asn Leu Ile Gly Ser Phe Asn Leu Leu Arg Leu Ala Ala Ala Ala
        115                 120                 125

Met Ala Glu Gly Ala Ala Asp Glu Ser Gly Glu Arg Gly Val Ile Ile
    130                 135                 140

Asn Thr Ala Ser Ile Ala Ala Tyr Asp Gly Gln Ile Gly Gln Ala Ala
145                 150                 155                 160

Tyr Ala Ala Ser Lys Gly Ala Ile Ala Ser Leu Thr Leu Pro Ala Ala
                165                 170                 175

Arg Glu Leu Ala Arg Phe Gly Ile Arg Val Met Thr Ile Ala Pro Gly
            180                 185                 190

Ile Phe Glu Thr Pro Met Met Ala Gly Met Ser Asp Glu Val Arg Ala
        195                 200                 205

Ser Leu Ala Ala Gly Val Pro Phe Pro Pro Arg Leu Gly Arg Pro Gln
    210                 215                 220
```

Glu Tyr Ala Ala Leu Ala Arg His Ile Ile Glu Asn Ser Met Leu Asn
225                 230                 235                 240

Gly Glu Val Ile Arg Leu Asp Gly Ala Leu Arg Met Ala Ala Lys
            245                 250                 255

<210> SEQ ID NO 20
<211> LENGTH: 1194
<212> TYPE: DNA
<213> ORGANISM: Pseudomonas putida

<400> SEQUENCE: 20

| | | | | | |
|---|---|---|---|---|---|
| atgaccctcg | ccaatgaccc | catcgttatc | gtcagcgccg | tgcgcacgcc | catgggcggg | 60 |
| ttgcagggcg | acctcaagag | cctgactgcg | ccgcaactgg | gcagcgccgc | cattcgtgct | 120 |
| gccgtggaac | gggccggcat | cgatgccgcc | ggtgtcgagc | aggtactgtt | cggctgcgtg | 180 |
| ctgccggccg | gccagggcca | ggcaccggca | cgccaggccg | cgctgggcgc | cgggctggac | 240 |
| aagcacacca | cctgcaccac | cctgaacaag | atgtgcggct | cgggtatgca | agccgcgatc | 300 |
| atggcccatg | acctgctgct | ggccggcacc | gcagacgtgg | tagtggcggg | tggcatggaa | 360 |
| agcatgacca | acgcgccgta | cctgctggac | aaagcccgtg | gcggctaccg | catgggccac | 420 |
| ggcaagatca | tcgaccacat | gttcatggac | ggtctcgaag | acgcctacga | caaaggccgc | 480 |
| ctgatgggta | cctttgccga | ggactgtgcc | caggccaatg | ccttcagccg | cgaggcccag | 540 |
| gaccagttcg | ccatcgcctc | gctgacccga | gcgcaggaag | ccatcagcag | cggccgtttt | 600 |
| gccgccgaga | tcgtgccggt | ggaagtcacc | gagggcaagg | aaaagcgcgt | catcaaggat | 660 |
| gacgagcagc | cgcccaaggc | gcgtctggac | aagattgcgc | agctcaaacc | ggcgtttcgt | 720 |
| gaaggcggca | ccgtgacggc | ggccaacgcc | agttcgattt | ccgacggcgc | tgcggcgctg | 780 |
| gtactgatgc | gccgctccga | ggccgacaaa | cgtggcctca | agccattggc | cgtcatccac | 840 |
| ggccacgccg | cctttgccga | cacccccggcg | ctgttcccga | ccgccccgat | cggcgcgatc | 900 |
| gacaaactga | tgaaacgcac | cggctggaac | ctggccgaag | tcgacctgtt | cgagatcaac | 960 |
| gaggcctttcg | ccgtggtcac | cctggcggcc | atgaaacacc | tcgacctgcc | acacgacaag | 1020 |
| gtcaatatcc | acgcggcgc | ctgcgccctc | ggtcacccga | tcggcgcttc | tggcgcacgt | 1080 |
| attctggtca | ccctgttgtc | ggccttgcgc | cagaacaatc | tgcgtcgggg | tgtggcggcc | 1140 |
| atctgcatcg | gcggtggcga | ggccacggcc | atggctgttg | aatgcctgta | ctga | 1194 |

<210> SEQ ID NO 21
<211> LENGTH: 397
<212> TYPE: PRT
<213> ORGANISM: Pseudomonas putida

<400> SEQUENCE: 21

Met Thr Leu Ala Asn Asp Pro Ile Val Ile Val Ser Ala Val Arg Thr
1               5                   10                  15

Pro Met Gly Gly Leu Gln Gly Asp Leu Lys Ser Leu Thr Ala Pro Gln
            20                  25                  30

Leu Gly Ser Ala Ala Ile Arg Ala Ala Val Glu Arg Ala Gly Ile Asp
        35                  40                  45

Ala Ala Gly Val Glu Gln Val Leu Phe Gly Cys Val Leu Pro Ala Gly
    50                  55                  60

Gln Gly Gln Ala Pro Ala Arg Gln Ala Ala Leu Gly Ala Gly Leu Asp
65                  70                  75                  80

Lys His Thr Thr Cys Thr Thr Leu Asn Lys Met Cys Gly Ser Gly Met

```
                        85                  90                  95
Gln Ala Ala Ile Met Ala His Asp Leu Leu Ala Gly Thr Ala Asp
                100                 105                 110
Val Val Ala Gly Gly Met Glu Ser Met Thr Asn Ala Pro Tyr Leu
                115                 120                 125
Leu Asp Lys Ala Arg Gly Tyr Arg Met Gly His Gly Lys Ile Ile
                130                 135                 140
Asp His Met Phe Met Asp Gly Leu Glu Asp Ala Tyr Asp Lys Gly Arg
145                 150                 155                 160
Leu Met Gly Thr Phe Ala Glu Asp Cys Ala Gln Ala Asn Ala Phe Ser
                165                 170                 175
Arg Glu Ala Gln Asp Gln Phe Ala Ile Ala Ser Leu Thr Arg Ala Gln
                180                 185                 190
Glu Ala Ile Ser Ser Gly Arg Phe Ala Ala Glu Ile Val Pro Val Glu
                195                 200                 205
Val Thr Glu Gly Lys Glu Lys Arg Val Ile Lys Asp Asp Glu Gln Pro
210                 215                 220
Pro Lys Ala Arg Leu Asp Lys Ile Ala Gln Leu Lys Pro Ala Phe Arg
225                 230                 235                 240
Glu Gly Gly Thr Val Thr Ala Ala Asn Ala Ser Ser Ile Ser Asp Gly
                245                 250                 255
Ala Ala Ala Leu Val Leu Met Arg Arg Ser Glu Ala Asp Lys Arg Gly
                260                 265                 270
Leu Lys Pro Leu Ala Val Ile His Gly His Ala Ala Phe Ala Asp Thr
                275                 280                 285
Pro Ala Leu Phe Pro Thr Ala Pro Ile Gly Ala Ile Asp Lys Leu Met
290                 295                 300
Lys Arg Thr Gly Trp Asn Leu Ala Glu Val Asp Leu Phe Glu Ile Asn
305                 310                 315                 320
Glu Ala Phe Ala Val Val Thr Leu Ala Ala Met Lys His Leu Asp Leu
                325                 330                 335
Pro His Asp Lys Val Asn Ile His Gly Gly Ala Cys Ala Leu Gly His
                340                 345                 350
Pro Ile Gly Ala Ser Gly Ala Arg Ile Leu Val Thr Leu Leu Ser Ala
                355                 360                 365
Leu Arg Gln Asn Asn Leu Arg Arg Gly Val Ala Ala Ile Cys Ile Gly
                370                 375                 380
Gly Gly Glu Ala Thr Ala Met Ala Val Glu Cys Leu Tyr
385                 390                 395

<210> SEQ ID NO 22
<211> LENGTH: 1128
<212> TYPE: DNA
<213> ORGANISM: Pseudomonas putida

<400> SEQUENCE: 22
atgctggtaa atgacgagca acaacagatc gccgacgcgg tacgtgcgtt cgcccaggaa      60
cgcctgaagc cgtttgccga gcaatgggac aaggaccatc gcttcccgaa agaggccatc     120
gacgagatgg ccgaactggg cctgttcggc atgctggtgc cggagcagtg gggcggtagc     180
gacaccggtt atgtggccta tgccatggcc ttggaggaaa tcgctgcggg cgatggcgcc     240
tgctcgacca tcatgagcgt gcacaactcg gtgggttgcg tgccgatcct cgcttcggc     300 aacgagcagc agaaagagca gttcctcacc ccgctggcga caggtgcgat gctcggtgct     360
```

```
ttcgccctga ccgagccgca ggctggctcc gatgccagca gcctgaagac ccgcgcacgc    420
ctggaaggcg accattacgt gctcaatggc agcaagcagt tcattacctc ggggcagaac    480
gccggcgtag tgatcgtgtt tgcggtcacc gacccggagg ccggcaagcg tggcatcagc    540
gccttcatcg tgccgaccga ttcgccgggc taccaggtag cgcgggtgga ggacaaactc    600
ggccagcacg cctccgacac ctgccagatc gtttcgaca  atgtgcaagt gccagtggcc    660
aaccggctgg gggcggaggg tgaaggctac aagatcgccc tggccaacct tgaaggcggc    720
cgtatcggca tcgcctcgca agcggtgggt atggcccgcg cggcgttcga agtggcgcgg    780
gactatgcca acgagcgcca gagctttggc aaaccgctga tcgagcacca ggccgtggcg    840
tttcgcctgg ccgacatggc aacgaaaatt tccgttgccc ggcagatggt attgcacgcc    900
gctgcccttc gtgatgcggg cgcccggcg ctggtggaag cgtcgatggc caagctgttc     960
gcctcggaaa tggccgaaaa ggtctgttcg gacgccttgc agaccctggg cggttatggc   1020
tatctgagtg acttcccgct ggagcggatc taccgcgacg ttcgggtttg ccagatctac   1080
gaaggcacca gcgacattca gcgcatggtc attgcgcgca tctttga                 1128
```

<210> SEQ ID NO 23
<211> LENGTH: 375
<212> TYPE: PRT
<213> ORGANISM: Pseudomonas putida

<400> SEQUENCE: 23

```
Met Leu Val Asn Asp Glu Gln Gln Ile Ala Asp Ala Val Arg Ala
1               5                   10                  15

Phe Ala Gln Glu Arg Leu Lys Pro Phe Ala Glu Gln Trp Asp Lys Asp
            20                  25                  30

His Arg Phe Pro Lys Glu Ala Ile Asp Glu Met Ala Glu Leu Gly Leu
        35                  40                  45

Phe Gly Met Leu Val Pro Glu Gln Trp Gly Gly Ser Asp Thr Gly Tyr
    50                  55                  60

Val Ala Tyr Ala Met Ala Leu Glu Glu Ile Ala Ala Gly Asp Gly Ala
65                  70                  75                  80

Cys Ser Thr Ile Met Ser Val His Asn Ser Val Gly Cys Val Pro Ile
                85                  90                  95

Leu Arg Phe Gly Asn Glu Gln Gln Lys Glu Gln Phe Leu Thr Pro Leu
            100                 105                 110

Ala Thr Gly Ala Met Leu Gly Ala Phe Ala Leu Thr Glu Pro Gln Ala
        115                 120                 125

Gly Ser Asp Ala Ser Ser Leu Lys Thr Arg Ala Arg Leu Glu Gly Asp
    130                 135                 140

His Tyr Val Leu Asn Gly Ser Lys Gln Phe Ile Thr Ser Gly Gln Asn
145                 150                 155                 160

Ala Gly Val Val Ile Val Phe Ala Val Thr Asp Pro Glu Ala Gly Lys
                165                 170                 175

Arg Gly Ile Ser Ala Phe Ile Val Pro Thr Asp Ser Pro Gly Tyr Gln
            180                 185                 190

Val Ala Arg Val Glu Asp Lys Leu Gly Gln His Ala Ser Asp Thr Cys
        195                 200                 205

Gln Ile Val Phe Asp Asn Val Gln Val Pro Val Ala Asn Arg Leu Gly
    210                 215                 220

Ala Glu Gly Glu Gly Tyr Lys Ile Ala Leu Ala Asn Leu Glu Gly Gly
225                 230                 235                 240
```

```
Arg Ile Gly Ile Ala Ser Gln Ala Val Gly Met Ala Arg Ala Phe
                245                 250                 255

Glu Val Ala Arg Asp Tyr Ala Asn Glu Arg Gln Ser Phe Gly Lys Pro
            260                 265                 270

Leu Ile Glu His Gln Ala Val Ala Phe Arg Leu Ala Asp Met Ala Thr
        275                 280                 285

Lys Ile Ser Val Ala Arg Gln Met Val Leu His Ala Ala Leu Arg
    290                 295                 300

Asp Ala Gly Arg Pro Ala Leu Val Glu Ala Ser Met Ala Lys Leu Phe
305                 310                 315                 320

Ala Ser Glu Met Ala Glu Lys Val Cys Ser Asp Ala Leu Gln Thr Leu
            325                 330                 335

Gly Gly Tyr Gly Tyr Leu Ser Asp Phe Pro Leu Glu Arg Ile Tyr Arg
        340                 345                 350

Asp Val Arg Val Cys Gln Ile Tyr Glu Gly Thr Ser Asp Ile Gln Arg
    355                 360                 365

Met Val Ile Ala Arg Asn Leu
    370                 375

<210> SEQ ID NO 24
<211> LENGTH: 774
<212> TYPE: DNA
<213> ORGANISM: Pseudomonas putida

<400> SEQUENCE: 24
atggcattcg aaaccatcct gttggacatc cacggcaagg ttggcctgat caccctcaac        60
cggccgcagg cgctcaatgc gctgaacgcg cagattgtcg gcgagatcaa ccaggctctg       120
gaccagctcg agcgcgaccc gaacatcggc tgcgtggtgc tgacaggctc ggccaaagcc       180
tttgccgctg gcgccgacat caaggaaatg gccgagctgc aatacccgca gatctacgtc       240
gacgacctgt tcagcgacgc tgaccgcatc gccaatcgcc gtaagccgat cattgctgct       300
gtgtctggat ttgccttggg cggcggctgt gagctggcga tgatgtgcga ctttatcctc       360
gctgcggaca atgccaaatt tggtcaaccg gaaatcaacc tgggcgtgct gccgggcatg       420
ggcggcaccc agcgcctgac gcgtgcggtg gcaaggcca aggccatgga gctttgcctg        480
accggccgcc tgatgggcgc ggaagaagcc gagcgtgcag gcctggtggc gcggatcgtg       540
ccgcaggcag agctggtgga agaggcgctg aaggtggcgg cgaccattgc cagcaagtcg       600
attccggtga gcatgatggt caaggagagc gtcaaccggg catttgaagt caccctcagc       660
gagggggttc gctttgagcg tcgggtcttc catgcggctt tctccaccga agaccagaaa       720
gaaggcatgg ccgcattcat cgccaagcgt gaggcacagt tcaaggaccg ttga            774

<210> SEQ ID NO 25
<211> LENGTH: 257
<212> TYPE: PRT
<213> ORGANISM: Pseudomonas putida

<400> SEQUENCE: 25

Met Ala Phe Glu Thr Ile Leu Leu Asp Ile His Gly Lys Val Gly Leu
1               5                   10                  15

Ile Thr Leu Asn Arg Pro Gln Ala Leu Asn Ala Leu Asn Ala Gln Ile
            20                  25                  30

Val Gly Glu Ile Asn Gln Ala Leu Asp Gln Leu Glu Arg Asp Pro Asn
        35                  40                  45

Ile Gly Cys Val Val Leu Thr Gly Ser Ala Lys Ala Phe Ala Ala Gly
```

```
            50                  55                  60
Ala Asp Ile Lys Glu Met Ala Glu Leu Gln Tyr Pro Gln Ile Tyr Val
 65                  70                  75                  80

Asp Asp Leu Phe Ser Asp Ala Asp Arg Ile Ala Asn Arg Arg Lys Pro
                 85                  90                  95

Ile Ile Ala Ala Val Ser Gly Phe Ala Leu Gly Gly Cys Glu Leu
                100                 105                 110

Ala Met Met Cys Asp Phe Ile Leu Ala Ala Asp Asn Ala Lys Phe Gly
            115                 120                 125

Gln Pro Glu Ile Asn Leu Gly Val Leu Pro Gly Met Gly Gly Thr Gln
        130                 135                 140

Arg Leu Thr Arg Ala Val Gly Lys Ala Lys Ala Met Glu Leu Cys Leu
145                 150                 155                 160

Thr Gly Arg Leu Met Gly Ala Glu Glu Ala Arg Ala Gly Leu Val
                165                 170                 175

Ala Arg Ile Val Pro Gln Ala Glu Leu Val Glu Glu Ala Leu Lys Val
                180                 185                 190

Ala Ala Thr Ile Ala Ser Lys Ser Ile Pro Val Ser Met Met Val Lys
                195                 200                 205

Glu Ser Val Asn Arg Ala Phe Glu Val Thr Leu Ser Glu Gly Val Arg
        210                 215                 220

Phe Glu Arg Arg Val Phe His Ala Ala Phe Ser Thr Glu Asp Gln Lys
225                 230                 235                 240

Glu Gly Met Ala Ala Phe Ile Ala Lys Arg Glu Ala Gln Phe Lys Asp
                245                 250                 255

Arg
```

<210> SEQ ID NO 26
<211> LENGTH: 1302
<212> TYPE: DNA
<213> ORGANISM: Pseudomonas putida

<400> SEQUENCE: 26

```
atggccaaac ttgccttgga gcaggccatt gcgccggagt gggtcgatca ggttttcgag    60
gagcaccgcc aacggcagta ttctcgcgag ctgctgttct cgaccattat caagttgatg   120
tcgcttgttt cattgggctt gaagccatcg ctgcatgctg cggcaagaca actgacgac    180
cttcccgtca gcctggcagc tctgtacgac aagatcagtc gaaccgaacc tgccctgttg   240
cgtgctctgg tgacaggctg cgcgcagcgc ttggcgccga caatccatga gttgggctgc   300
tcagccatgc ttcctgattg caagttcgg gtggtcgatg cagccactt ggcctctacc     360
gaaaagcgtc ttggcgcgtt gcgccaagag cgcggagcgg ctcgcccgg ttttcggtg     420
gtggtttacg accccgacct ggatcaggta attgacctcc agccgtgcga ggacgcctac   480
gcaagcgaac gagtttgtgt tttgccgttg ctggctgaag caagaccaa tcaggtttgg    540
atcgctgacc gtctctactg cacgctgcct gtaatggagg cgtgcgaaca ggtgaagaca   600
tcatttgtca ttcgccagca ggccaagcat ccacgcttga tccaggaagg tgagtggcaa   660
gcaccgatgc ccgtcgccac aggcactgtg cgcgagcaat ccatcgaagt aaaaggcggg   720
caccgctggc gacgtgtcga gttaacgctt cattcaccaa acgactcagg tgataacagc   780
ttgatgttct ggagcaacct gcccgagagc atcagtgcgc aacagatcgc agacttctat   840
cggcgccgct ggagcattga agggatgttc cagcggttgg aagcaattct ggaaagtgaa   900
attgaaaccc tcggcagtcc gcgagccgcc ttgcttggat tcaccactgc cgtgctggca   960
```

```
tacaacgttc tggccttgct caagcgaagt gttgaacagg ctcaccgcga tgccttgccc    1020
gagaattggg aagcctcgat ctatcacttg gcggtgcaga tcagaggggg ttacgaaggc    1080
atgcagattg ccctgccatc cgagtacatg cccgttgttc cgatggaaaa cctggctcag    1140
cgcctgctgg agctggccag aaacatccag cccagacagg ttgcgaaaag cccacgaggc    1200
cccaaggtgc tcaaagctaa ggcctgggtg caagggacgg ctgtacatgc tcatgtttcg    1260
acggatcggg tcatcaaagc cgccaaaacc aaaagacctt ga                      1302
```

<210> SEQ ID NO 27
<211> LENGTH: 433
<212> TYPE: PRT
<213> ORGANISM: Pseudomonas putida

<400> SEQUENCE: 27

```
Met Ala Lys Leu Ala Leu Glu Gln Ala Ile Ala Pro Glu Trp Val Asp
1               5                   10                  15

Gln Val Phe Glu Glu His Arg Gln Arg Gln Tyr Ser Arg Glu Leu Leu
            20                  25                  30

Phe Ser Thr Ile Ile Lys Leu Met Ser Leu Val Ser Leu Gly Leu Lys
        35                  40                  45

Pro Ser Leu His Ala Ala Ala Arg Gln Leu Asp Asp Leu Pro Val Ser
    50                  55                  60

Leu Ala Ala Leu Tyr Asp Lys Ile Ser Arg Thr Glu Pro Ala Leu Leu
65                  70                  75                  80

Arg Ala Leu Val Thr Gly Cys Ala Gln Arg Leu Ala Pro Thr Ile His
                85                  90                  95

Glu Leu Gly Cys Ser Ala Met Leu Pro Asp Trp Gln Val Arg Val Val
            100                 105                 110

Asp Gly Ser His Leu Ala Ser Thr Glu Lys Arg Leu Gly Ala Leu Arg
        115                 120                 125

Gln Glu Arg Gly Ala Ala Arg Pro Gly Phe Ser Val Val Val Tyr Asp
    130                 135                 140

Pro Asp Leu Asp Gln Val Ile Asp Leu Gln Pro Cys Glu Asp Ala Tyr
145                 150                 155                 160

Ala Ser Glu Arg Val Cys Val Leu Pro Leu Leu Ala Glu Ala Lys Thr
                165                 170                 175

Asn Gln Val Trp Ile Ala Asp Arg Leu Tyr Cys Thr Leu Pro Val Met
            180                 185                 190

Glu Ala Cys Glu Gln Val Lys Thr Ser Phe Val Ile Arg Gln Gln Ala
        195                 200                 205

Lys His Pro Arg Leu Ile Gln Glu Gly Glu Trp Gln Ala Pro Met Pro
    210                 215                 220

Val Ala Thr Gly Thr Val Arg Glu Gln Ser Ile Glu Val Lys Gly Gly
225                 230                 235                 240

His Arg Trp Arg Arg Val Glu Leu Thr Leu His Ser Pro Asn Asp Ser
                245                 250                 255

Gly Asp Asn Ser Leu Met Phe Trp Ser Asn Leu Pro Glu Ser Ile Ser
            260                 265                 270

Ala Gln Gln Ile Ala Asp Phe Tyr Arg Arg Trp Ser Ile Glu Gly
        275                 280                 285

Met Phe Gln Arg Leu Glu Ala Ile Leu Glu Ser Glu Ile Glu Thr Leu
    290                 295                 300

Gly Ser Pro Arg Ala Ala Leu Leu Gly Phe Thr Thr Ala Val Leu Ala
```

```
                305                 310                 315                 320
Tyr Asn Val Leu Ala Leu Leu Lys Arg Ser Val Glu Gln Ala His Arg
                    325                 330                 335

Asp Ala Leu Pro Glu Asn Trp Glu Ala Ser Ile Tyr His Leu Ala Val
                340                 345                 350

Gln Ile Arg Gly Gly Tyr Glu Gly Met Gln Ile Ala Leu Pro Ser Glu
            355                 360                 365

Tyr Met Pro Val Val Pro Met Glu Asn Leu Ala Gln Arg Leu Leu Glu
        370                 375                 380

Leu Ala Arg Asn Ile Gln Pro Arg Gln Val Ala Lys Ser Pro Arg Gly
385                 390                 395                 400

Pro Lys Val Leu Lys Ala Lys Ala Trp Val Gln Gly Thr Ala Val His
                405                 410                 415

Ala His Val Ser Thr Asp Arg Val Ile Lys Ala Ala Lys Thr Lys Arg
                420                 425                 430

Pro

<210> SEQ ID NO 28
<211> LENGTH: 369
<212> TYPE: DNA
<213> ORGANISM: Pseudomonas putida

<400> SEQUENCE: 28
atgcccgtca cctgcctccg caaggcctgc gttcggcctc ctgaagtcgc gaagatcaag      60
atcaagatca agatcaagat caagatcaag atcaagatca agatcaacgg caacggcaac     120
ggcaacggca acggcaacgg caacggcaac ggcaacagca ggtggatggg cacagaatct     180
cagtttacta ctggcacagc agctgagctg gggtgccgac cggcggattg tgagcagtgg     240
aagcaaattc gcacccattt gcagttgctc cacgcggcgt ggcgccttag actgccgccc     300
cctgtaaaag agtgccggtt ggcgcttgaa gaattccgct ggcgatgcat aggcatcgac     360
ggcacatga                                                             369

<210> SEQ ID NO 29
<211> LENGTH: 122
<212> TYPE: PRT
<213> ORGANISM: Pseudomonas putida

<400> SEQUENCE: 29

Met Pro Val Thr Cys Leu Arg Lys Ala Cys Val Arg Pro Pro Glu Val
1               5                   10                  15

Ala Lys Ile Lys Ile Lys Ile Lys Ile Lys Ile Lys Ile Lys Ile Lys
            20                  25                  30

Ile Lys Ile Asn Gly Asn Gly Asn Gly Asn Gly Asn Gly Asn Gly Asn
        35                  40                  45

Gly Asn Gly Asn Ser Arg Trp Met Gly Thr Glu Ser Gln Phe Thr Thr
    50                  55                  60

Gly Thr Ala Ala Glu Leu Gly Cys Arg Pro Ala Asp Cys Glu Gln Trp
65                  70                  75                  80

Lys Gln Ile Arg Thr His Leu Gln Leu Leu His Ala Ala Trp Arg Leu
                85                  90                  95

Arg Leu Pro Pro Pro Val Lys Glu Cys Arg Leu Ala Leu Glu Glu Phe
            100                 105                 110

Arg Trp Arg Cys Ile Gly Ile Asp Gly Thr
        115                 120
```

<210> SEQ ID NO 30
<211> LENGTH: 2448
<212> TYPE: DNA
<213> ORGANISM: Pseudomonas putida

<400> SEQUENCE: 30

| | |
|---|---|
| atgttgctgt tgtggttggt ggtgctggtg atcggcgcgg cgtacctcac gcaccggcgc | 60 |
| ctggcgccct tgcagattct cggcatcgtg gcggcctatg tgctgttgat gggcatttc | 120 |
| agcagtgccc ccggctggct gctggcgctg atctgggtgg tgctggccct gaagatcgcc | 180 |
| ctggttgcgc tcccgcagtg gcgacgcaaa ctctttaccg ccccggtatt ccgctggttc | 240 |
| cagcgcaccc tgccacccat gtcgcagacc gagcgcgaag ccatcgacgc cggtaccgtg | 300 |
| tggtgggacg cgaactgtt cagtggccgc cccgactggc gcaccttgct ggcctacccg | 360 |
| gcaccgaaac tgaccgaaga agaacaggcc ttcatcgatg gcccgaccga agcactgtgc | 420 |
| gccatggtca gcgactggca gattggccag gatctggacc tgccgcccga agcctgggca | 480 |
| catatcaagc aacatggctt tttcgccctg atcatcccca aggaatacgg cggcaagggc | 540 |
| ttctccgcct acgcccactc ccaggtggcg atgaagctgg ccaccggag cggcgacctg | 600 |
| gcctccacgg tgatggtgcc caactccctg ggccctgccg aactgctgct gcactacggc | 660 |
| accgacgaac aacgcaaccg ctacctgccg cgcctggccc gtggcgagga aatcccctgt | 720 |
| ttcgccctca ccgggccgct ggccggttcg acgctggcg ccatgcccga caccggcatc | 780 |
| atctgcaaag gccagtggca aggcgaagaa gtgatcggcc tgcgcctgaa ctgggaaaag | 840 |
| cgctacatca ccctcggccc ggtcgccacc ctgctgggcc tggccttcaa agcctacgac | 900 |
| cccgaccatc tgttgggcga acaggaggag ctcggcatca gcctggccct gatccccacc | 960 |
| gacacgcccg gcgtcgagat cggcaaacgc cacctgccgc tgggcgccgc cttcatgaac | 1020 |
| ggccccaaca gcggcaaaga cgtgttcgta ccgctggact tcctgatcgg tggccaggcc | 1080 |
| atgctcggca agggctggat gatgttgatg aactgcctgt cggtgggccg ctccatctca | 1140 |
| ctgccggcgg tcggcaccgg tgccgccaag tacaccagcc tggtgaccgg ccagtacgcc | 1200 |
| aatatccgcg agcagttcaa cgtgccattg gcggccttcg aaggcatcca ggaatcgctg | 1260 |
| gcacgcattg gcggcaacgc ctggctgatg acagtgccc gcctgctgac cgccaaggcc | 1320 |
| gtggacctgg cgaaaagcc ctcggtgctg tcggcgatcc tcaagtacca cctgaccgag | 1380 |
| cgtggccgcg aatgcatcca gcacgccatg gacgtgcacg gtggcaaggg catcatcatg | 1440 |
| ggcccgaaca actacctggg ccgcaactgg caaggtgcgc cgatcttcat acggtcgaa | 1500 |
| ggtgccaaca tcctttcacg caacctgatg atcttcggcc agggcgccat cgctgccat | 1560 |
| ccgttcgtgc tcaaggaaat ggcattggcc gggcgtgaag accacgatca ggcactcaag | 1620 |
| gaattcgatg acctgctgat gaaacacatc ctgttcgccg ccggcaatgc ggccagtacc | 1680 |
| ttggtctacg gcctggggct gggtcgcttt gagcgggtgc cgggcgatgc cctgagccaa | 1740 |
| ggctacttcc gcgccctgaa ccgccaggcg gcggcgtttg ccatgatggc cgacctttcg | 1800 |
| atgatgctgc tgggtggggc gctcaagcgc gcgagcgcc tcagcgcccg gcttggcgat | 1860 |
| gtgctgagct atctgtacct cgccagcgct gccctgaagc gctatcacga ccagggctcg | 1920 |
| cccgaatacc tgcagccgct gctgcgctgg gccatggaag aaagcctggg ccagacggag | 1980 |
| cgtgcgctgg accgcctgct cgacaatttc cccaaccgct tcgtcggctg cgcgctgcgg | 2040 |
| gtactggtgt tccccttcgg ccgccgccat aagggccccg tgatgaact ggatgccgag | 2100 |
| gtggccgagc tgatcggccg gcgcaagggc gatccggcac tggaggaact gctggccggc | 2160 |

```
tgctaccgcc cacaggcaga acacgacccg gtcgcggatc tgcaacgggc cagtgacctg    2220
ctcgaagaca cggcacagtt gagcaaggcc ctgtaccaag ccgtcaagga aggcaaagtc    2280
cagccagccc ccggccagtc cggtatcgac gccgccgtca aggcaggcgt gctgcaaccc    2340
gacgatggcc agcggctgca cgaggccgaa caggctcggc gcaaggtgat cgatgtcgat    2400
gccttcgaca aggcgcagtt gctcgccgta ccgggcaagg tgcgctga                 2448
```

<210> SEQ ID NO 31
<211> LENGTH: 815
<212> TYPE: PRT
<213> ORGANISM: Pseudomonas putida

<400> SEQUENCE: 31

```
Met Leu Leu Leu Trp Leu Val Leu Val Ile Gly Ala Ala Tyr Leu
1               5                   10                  15

Thr His Arg Arg Leu Ala Pro Leu Gln Ile Leu Gly Ile Val Ala Ala
                20                  25                  30

Tyr Val Leu Leu Met Gly Ile Phe Ser Ser Ala Pro Gly Trp Leu Leu
            35                  40                  45

Ala Leu Ile Trp Val Val Leu Ala Leu Lys Ile Ala Leu Val Ala Leu
50                  55                  60

Pro Gln Trp Arg Arg Lys Leu Phe Thr Ala Pro Val Phe Arg Trp Phe
65                  70                  75                  80

Gln Arg Thr Leu Pro Pro Met Ser Gln Thr Glu Arg Glu Ala Ile Asp
                85                  90                  95

Ala Gly Thr Val Trp Trp Asp Gly Glu Leu Phe Ser Arg Pro Asp
            100                 105                 110

Trp Arg Thr Leu Leu Ala Tyr Pro Ala Pro Lys Leu Thr Glu Glu Glu
        115                 120                 125

Gln Ala Phe Ile Asp Gly Pro Thr Glu Ala Leu Cys Ala Met Val Ser
    130                 135                 140

Asp Trp Gln Ile Gly Gln Asp Leu Asp Leu Pro Pro Glu Ala Trp Ala
145                 150                 155                 160

His Ile Lys Gln His Gly Phe Phe Ala Leu Ile Ile Pro Lys Glu Tyr
                165                 170                 175

Gly Gly Lys Gly Phe Ser Ala Tyr Ala His Ser Gln Val Ala Met Lys
            180                 185                 190

Leu Ala Thr Arg Ser Gly Asp Leu Ala Ser Thr Val Met Val Pro Asn
        195                 200                 205

Ser Leu Gly Pro Ala Glu Leu Leu His Tyr Gly Thr Asp Glu Gln
    210                 215                 220

Arg Asn Arg Tyr Leu Pro Arg Leu Ala Arg Gly Glu Glu Ile Pro Cys
225                 230                 235                 240

Phe Ala Leu Thr Gly Pro Leu Ala Gly Ser Asp Ala Gly Ala Met Pro
                245                 250                 255

Asp Thr Gly Ile Ile Cys Lys Gly Gln Trp Gly Glu Glu Val Ile
            260                 265                 270

Gly Leu Arg Leu Asn Trp Glu Lys Arg Tyr Ile Thr Leu Gly Pro Val
        275                 280                 285

Ala Thr Leu Leu Gly Leu Ala Phe Lys Ala Tyr Asp Pro Asp His Leu
    290                 295                 300

Leu Gly Glu Gln Glu Glu Leu Gly Ile Ser Leu Ala Leu Ile Pro Thr
305                 310                 315                 320
```

```
Asp Thr Pro Gly Val Glu Ile Gly Lys Arg His Leu Pro Leu Gly Ala
            325                 330                 335
Ala Phe Met Asn Gly Pro Asn Ser Gly Lys Asp Val Phe Val Pro Leu
        340                 345                 350
Asp Phe Leu Ile Gly Gly Gln Ala Met Leu Gly Lys Gly Trp Met Met
        355                 360                 365
Leu Met Asn Cys Leu Ser Val Gly Arg Ser Ile Ser Leu Pro Ala Val
    370                 375                 380
Gly Thr Gly Ala Ala Lys Tyr Thr Ser Leu Val Thr Gly Gln Tyr Ala
385                 390                 395                 400
Asn Ile Arg Glu Gln Phe Asn Val Pro Leu Ala Ala Phe Glu Gly Ile
                405                 410                 415
Gln Glu Ser Leu Ala Arg Ile Gly Gly Asn Ala Trp Leu Met Asp Ser
            420                 425                 430
Ala Arg Leu Leu Thr Ala Lys Ala Val Asp Leu Gly Glu Lys Pro Ser
        435                 440                 445
Val Leu Ser Ala Ile Leu Lys Tyr His Leu Thr Glu Arg Gly Arg Glu
    450                 455                 460
Cys Ile Gln His Ala Met Asp Val His Gly Lys Gly Ile Ile Met
465                 470                 475                 480
Gly Pro Asn Asn Tyr Leu Gly Arg Asn Trp Gln Gly Ala Pro Ile Phe
                485                 490                 495
Ile Thr Val Glu Gly Ala Asn Ile Leu Ser Arg Asn Leu Met Ile Phe
            500                 505                 510
Gly Gln Gly Ala Ile Arg Cys His Pro Phe Val Leu Lys Glu Met Ala
        515                 520                 525
Leu Ala Gly Arg Glu Asp His Asp Gln Ala Leu Lys Glu Phe Asp Asp
    530                 535                 540
Leu Leu Met Lys His Ile Leu Phe Ala Ala Gly Asn Ala Ala Ser Thr
545                 550                 555                 560
Leu Val Tyr Gly Leu Gly Leu Gly Arg Phe Glu Arg Val Pro Gly Asp
                565                 570                 575
Ala Leu Ser Gln Gly Tyr Phe Arg Ala Leu Asn Arg Gln Ala Ala Ala
            580                 585                 590
Phe Ala Met Met Ala Asp Leu Ser Met Met Leu Leu Gly Gly Ala Leu
        595                 600                 605
Lys Arg Arg Glu Arg Leu Ser Ala Arg Leu Gly Asp Val Leu Ser Tyr
    610                 615                 620
Leu Tyr Leu Ala Ser Ala Ala Leu Lys Arg Tyr His Asp Gln Gly Ser
625                 630                 635                 640
Pro Glu Tyr Leu Gln Pro Leu Leu Arg Trp Ala Met Glu Glu Ser Leu
                645                 650                 655
Gly Gln Thr Glu Arg Ala Leu Asp Arg Leu Leu Asp Asn Phe Pro Asn
            660                 665                 670
Arg Phe Val Gly Cys Ala Leu Arg Val Leu Val Phe Pro Phe Gly Arg
        675                 680                 685
Arg His Lys Gly Pro Gly Asp Glu Leu Asp Ala Glu Val Ala Glu Leu
    690                 695                 700
Ile Gly Arg Arg Lys Gly Asp Pro Ala Leu Glu Leu Leu Ala Gly
705                 710                 715                 720
Cys Tyr Arg Pro Gln Ala Glu His Asp Pro Val Ala Asp Leu Gln Arg
                725                 730                 735
Ala Ser Asp Leu Leu Glu Asp Thr Ala Gln Leu Ser Lys Ala Leu Tyr
```

```
                    740                 745                 750
Gln Ala Val Lys Glu Gly Lys Val Gln Pro Ala Pro Gly Gln Ser Gly
            755                 760                 765

Ile Asp Ala Ala Val Lys Ala Gly Val Leu Gln Pro Asp Asp Gly Gln
        770                 775                 780

Arg Leu His Glu Ala Glu Gln Ala Arg Arg Lys Val Ile Asp Val Asp
785                 790                 795                 800

Ala Phe Asp Lys Ala Gln Leu Leu Ala Val Pro Gly Lys Val Arg
                805                 810                 815

<210> SEQ ID NO 32
<211> LENGTH: 1896
<212> TYPE: DNA
<213> ORGANISM: Pseudomonas putida

<400> SEQUENCE: 32
```

| | | | | | |
|---|---|---|---|---|---|
| atgacaataa | gatcgctacc | cgcccttccc | ccgctggccc | tgagcgtgcg | cgtcctgctg | 60 |
| atggccggta | gcctggccct | gggcaatgtg | caacagcgg | ccagcacacc | cgctgcacct | 120 |
| gccggcaaga | acgtcacctg | gaagacatc | gccaatgacc | acctgaccac | ccaggacgtg | 180 |
| ctgcagtacg | gcatgggcac | caatgcccag | cgctggagcc | cgctggccca | ggtcaatgac | 240 |
| aagaacgtgt | tcaagctgac | cccggcctgg | tcctactcct | tcggcgacga | aagcagcgc | 300 |
| ggccaggaat | cccaggccat | cgtcagcgat | ggcgtggtct | acgtcaccgg | ttcgtactca | 360 |
| cgggtattcg | ccctcgatgc | caagaccggc | aaacgcctgt | ggacctacaa | ccaccgcctg | 420 |
| cccgacaaca | ttcgtccctg | ctgcgacgtg | gtcaaccgcg | gggcggcgat | ctacggcgac | 480 |
| aagatctact | ttggcaccct | cgatgcgcgt | gtcatcgccc | tcgacaagcg | caccggcaaa | 540 |
| gtggtgtgga | caagaagtt | cggcgaccac | agcgccggct | acaccatgac | cggtgcgcca | 600 |
| gtgctgatca | aggacaagac | cagcggcaag | gtgctgctga | tccacggcag | ctccggcgat | 660 |
| gaattcggcg | tggtcggcca | gctgttcgcg | cgcgacccgg | acaccggtga | agaagtgtgg | 720 |
| atgcggccct | tcgtggaggg | ccacatgggc | cgcctgaacg | gcaaggacag | caccccgacc | 780 |
| ggtgacgtca | aggcgccgtc | ctggccagac | gaccctacca | ccgaaaccgg | caaggtcgaa | 840 |
| gcctggagcc | acggcggcgg | tgcccccttgg | caaagcgcga | gcttcgaccc | cgaaaccaac | 900 |
| accatcattg | tcgcgctgg | caaccccggc | ccttggaata | cctgggcgcg | cacgtcgaag | 960 |
| gacggcaacc | cgcatgactt | cgacagcctg | tacacctccg | gccaggtcgg | cgtcgacccg | 1020 |
| agcaccggcg | aggtcaagtg | gttctaccag | cacacccca | acgatgcctg | ggacttctcc | 1080 |
| ggcaacaacg | agctggtgct | gttcgactac | aaggacaaga | acggcaacgt | ggtcaaggcc | 1140 |
| accgcccacg | ccgaccgcaa | cggtttcttc | tatgtggttg | accgcaacaa | cggcaagctg | 1200 |
| caaaacgctt | tccccttcgt | cgacaacatc | acctgggcca | gccatatcga | cctgaagacc | 1260 |
| gggcgcccgg | tggaaaaccc | cggccaacgc | ccggccaagc | gctgccgggg | tgaaaccaag | 1320 |
| ggcaagccgg | tggaagtctc | gccaccgttc | ctgggcggca | gaactggaa | ccccatggcc | 1380 |
| tacagccagg | acaccgggct | gttctacatc | cccggcaacc | agtggaaaga | ggaatactgg | 1440 |
| accgaggaag | tgaactacaa | gaagggctcg | gcttatctgg | gcatgggctt | ccgtatcaag | 1500 |
| cgcatgtacg | acgaccacgt | cggcacgttg | gcgccatgg | acccgaccac | cggcaagctg | 1560 |
| gtgtgggaac | acaaggaaca | cctgccgtta | tgggccggtg | tgttggcgac | caagggcaac | 1620 |
| ctggtgttca | ccggcacggg | cgacggcttc | ttcaaggcct | cgacgccaa | gacgggcaaa | 1680 |
| gagctgtgga | agttccagac | cggcagcggc | atcgtctcgc | cgcccatcac | ctgggagcag | 1740 |

```
gacggcgagc agtacatcgg cgtgaccgtg ggctacggcg gtgcagtacc gctgtggggc    1800
ggcgacatgg ccgagctgac caaaccggtg gctcagggtg gttcgttctg ggtgttcaag    1860
atcccgagct gggacaacaa gactgcacaa cgttga                              1896
```

<210> SEQ ID NO 33
<211> LENGTH: 631
<212> TYPE: PRT
<213> ORGANISM: Pseudomonas putida

<400> SEQUENCE: 33

Met Thr Ile Arg Ser Leu Pro Ala Leu Ser Pro Leu Ala Leu Ser Val
1               5                   10                  15

Arg Val Leu Leu Met Ala Gly Ser Leu Ala Leu Gly Asn Val Ala Thr
            20                  25                  30

Ala Ala Ser Thr Pro Ala Ala Pro Ala Gly Lys Asn Val Thr Trp Glu
        35                  40                  45

Asp Ile Ala Asn Asp His Leu Thr Thr Gln Asp Val Leu Gln Tyr Gly
    50                  55                  60

Met Gly Thr Asn Ala Gln Arg Trp Ser Pro Leu Ala Gln Val Asn Asp
65                  70                  75                  80

Lys Asn Val Phe Lys Leu Thr Pro Ala Trp Ser Tyr Ser Phe Gly Asp
                85                  90                  95

Glu Lys Gln Arg Gly Gln Glu Ser Gln Ala Ile Val Ser Asp Gly Val
            100                 105                 110

Val Tyr Val Thr Gly Ser Tyr Ser Arg Val Phe Ala Leu Asp Ala Lys
        115                 120                 125

Thr Gly Lys Arg Leu Trp Thr Tyr Asn His Arg Leu Pro Asp Asn Ile
    130                 135                 140

Arg Pro Cys Cys Asp Val Val Asn Arg Gly Ala Ala Ile Tyr Gly Asp
145                 150                 155                 160

Lys Ile Tyr Phe Gly Thr Leu Asp Ala Arg Val Ile Ala Leu Asp Lys
                165                 170                 175

Arg Thr Gly Lys Val Val Trp Asn Lys Lys Phe Gly Asp His Ser Ala
            180                 185                 190

Gly Tyr Thr Met Thr Gly Ala Pro Val Leu Ile Lys Asp Lys Thr Ser
        195                 200                 205

Gly Lys Val Leu Leu Ile His Gly Ser Ser Gly Asp Glu Phe Gly Val
    210                 215                 220

Val Gly Gln Leu Phe Ala Arg Asp Pro Asp Thr Gly Glu Glu Val Trp
225                 230                 235                 240

Met Arg Pro Phe Val Glu Gly His Met Gly Arg Leu Asn Gly Lys Asp
                245                 250                 255

Ser Thr Pro Thr Gly Asp Val Lys Ala Pro Ser Trp Pro Asp Asp Pro
            260                 265                 270

Thr Thr Glu Thr Gly Lys Val Glu Ala Trp Ser His Gly Gly Gly Ala
        275                 280                 285

Pro Trp Gln Ser Ala Ser Phe Asp Pro Glu Thr Asn Thr Ile Ile Val
    290                 295                 300

Gly Ala Gly Asn Pro Gly Pro Trp Asn Thr Ala Arg Thr Ser Lys
305                 310                 315                 320

Asp Gly Asn Pro His Asp Phe Asp Ser Leu Tyr Thr Ser Gly Gln Val
                325                 330                 335

Gly Val Asp Pro Ser Thr Gly Glu Val Lys Trp Phe Tyr Gln His Thr

|   |   |   | 340 |   |   |   | 345 |   |   |   | 350 |   |
|---|---|---|---|---|---|---|---|---|---|---|---|---|

Pro Asn Asp Ala Trp Asp Phe Ser Gly Asn Asn Glu Leu Val Leu Phe
                355                 360                 365

Asp Tyr Lys Asp Lys Asn Gly Asn Val Val Lys Ala Thr Ala His Ala
        370                 375                 380

Asp Arg Asn Gly Phe Phe Tyr Val Val Asp Arg Asn Asn Gly Lys Leu
385                 390                 395                 400

Gln Asn Ala Phe Pro Phe Val Asp Asn Ile Thr Trp Ala Ser His Ile
                405                 410                 415

Asp Leu Lys Thr Gly Arg Pro Val Glu Asn Pro Gly Gln Arg Pro Ala
            420                 425                 430

Lys Pro Leu Pro Gly Glu Thr Lys Gly Lys Pro Val Glu Val Ser Pro
        435                 440                 445

Pro Phe Leu Gly Gly Lys Asn Trp Asn Pro Met Ala Tyr Ser Gln Asp
450                 455                 460

Thr Gly Leu Phe Tyr Ile Pro Gly Asn Gln Trp Lys Glu Glu Tyr Trp
465                 470                 475                 480

Thr Glu Glu Val Asn Tyr Lys Lys Gly Ser Ala Tyr Leu Gly Met Gly
                485                 490                 495

Phe Arg Ile Lys Arg Met Tyr Asp Asp His Val Gly Thr Leu Arg Ala
            500                 505                 510

Met Asp Pro Thr Thr Gly Lys Leu Val Trp Glu His Lys Glu His Leu
        515                 520                 525

Pro Leu Trp Ala Gly Val Leu Ala Thr Lys Gly Asn Leu Val Phe Thr
530                 535                 540

Gly Thr Gly Asp Gly Phe Pro Lys Ala Phe Asp Ala Lys Thr Gly Lys
545                 550                 555                 560

Glu Leu Trp Lys Phe Gln Thr Gly Ser Gly Ile Val Ser Pro Pro Ile
                565                 570                 575

Thr Trp Glu Gln Asp Gly Glu Gln Tyr Ile Gly Val Thr Val Gly Tyr
            580                 585                 590

Gly Gly Ala Val Pro Leu Trp Gly Gly Asp Met Ala Glu Leu Thr Lys
        595                 600                 605

Pro Val Ala Gln Gly Gly Ser Phe Trp Val Phe Lys Ile Pro Ser Trp
610                 615                 620

Asp Asn Lys Thr Ala Gln Arg
625                 630

<210> SEQ ID NO 34
<211> LENGTH: 1788
<212> TYPE: DNA
<213> ORGANISM: Pseudomonas putida

<400> SEQUENCE: 34

| atgacccgat | cccacgtcg | ccccttgttc | gccgtgagcc | tggtgctcag | cgccatgctg | 60 |
|---|---|---|---|---|---|---|
| cttgccggcg | cggctcacgc | cgctgtcagc | aatgaagaaa | tcctccagga | cccgaagaac | 120 |
| ccgcagcaga | tcgtgaccaa | tggcctgggc | gtgcagggcc | agcgctacag | cccgctggac | 180 |
| ctgctcaatg | tcaataacgt | caaggagctg | cgcccggtct | gggcgttctc | cttcggcggg | 240 |
| gagaagcagc | gcggccagca | ggcccagccg | ctgatcaagg | acggggtgat | gtacctgacc | 300 |
| ggctcctact | cgcgggtgtt | cgccgtggat | gcccgcaccg | gcaagaaact | gtggcaatac | 360 |
| gatgcacgtc | tgccgatga | catccgcccc | tgctgcgacg | taatcaaccg | cggcgtcgcg | 420 |
| ctgtacggca | acctggtgtt | cttcggcacg | ctggacgcca | agctggtggc | cctgaacaag | 480 |

```
gacaccggca aggtggtctg gagcaagaag gtcgccgacc acaaagaagg ctactccatc    540
agcgccgcgc cgatgatcgt caatggcaag ctgatcacag gcgttgccgg cggcgagttc    600
ggcgtggtgg gcaagatcca ggcgtacaac ccggagaacg gcgaactgct gtggatgcgc    660
cccaccgtgg aagggcacat gggctatgtg tacaaggatg gcaaggcgat cgagaacggt    720
atttccggcg gtgaggcggg caagacctgg cctggcgacc tgtggaagac cggcggcgcc    780
gcgccgtggc tgggggggtta ctacgaccct gaaaccaacc tgatcctgtt tggtaccggt    840
aacccggcgc cgtggaactc gcacctgcgc cccggtgaca acctgtactc ctcctcacgc    900
ctggcactga accggacga cggcaccatc aagtggcact ccagagcac gccgcatgac    960 ggctgggact cgacggcgt caacgagctg atctcgttca actacaagga cggcggcaag   1020
gaggtcaagg ctgccgccac ggcagaccgc aacggtttct tctacgtgct cgaccgcacc   1080
aacggcaagt tcatccgcgg cttccccttc gtggacaaga tcacctgggc cactggcctg   1140
gacaaggacg gccggccgat ctacaacgac gccagccgcc cgggcgcacc cggcagcgag   1200
gccaagggca gctcggtgtt cgtcgcgccg gccttcctcg gcgccaagaa ctggatgccg   1260
atggcctaca acaaggacac agggctgttc tacgtgccgt ccaacgagtg gggcatggac   1320
atctggaacg aaggcatcgc ctataagaaa ggtgcggcgt tcctcggtgc cggcttcacc   1380
atcaagccgc tcaatgaaga ctacatcggc gtgctgcgcg ccatcgaccc ggtcagcggc   1440
aaggaagtgt ggcgccacaa gaactatgcg ccgctgtggg gcggtgtgct gaccaccaag   1500
ggcaacctgg tgttcacggg cacgccagag ggcttcctgc aggcattcaa cgccaagacc   1560
ggcgacaagg tctgggaatt ccagaccggc tcgggcgtgc tcggctcgcc cgtcacctgg   1620
gaaatggacg gcgagcaata cgtttcggta gtctccggct ggggcggcgc ggtgccgctg   1680
tggggcggcg aagtggccaa cgggtcaagg acttcaacc agggcggcat gctctggacc   1740
ttcaagttgc ccaagcagtt gcagcaaacg gcaagcgtca agccataa               1788
```

<210> SEQ ID NO 35
<211> LENGTH: 595
<212> TYPE: PRT
<213> ORGANISM: Pseudomonas putida

<400> SEQUENCE: 35

```
Met Thr Arg Ser Pro Arg Arg Pro Leu Phe Ala Val Ser Leu Val Leu
1               5                   10                  15

Ser Ala Met Leu Leu Ala Gly Ala Ala His Ala Ala Val Ser Asn Glu
                20                  25                  30

Glu Ile Leu Gln Asp Pro Lys Asn Pro Gln Gln Ile Val Thr Asn Gly
            35                  40                  45

Leu Gly Val Gln Gly Gln Arg Tyr Ser Pro Leu Asp Leu Leu Asn Val
        50                  55                  60

Asn Asn Val Lys Glu Leu Arg Pro Val Trp Ala Phe Ser Phe Gly Gly
65                  70                  75                  80

Glu Lys Gln Arg Gly Gln Gln Ala Gln Pro Leu Ile Lys Asp Gly Val
                85                  90                  95

Met Tyr Leu Thr Gly Ser Tyr Ser Arg Val Phe Ala Val Asp Ala Arg
            100                 105                 110

Thr Gly Lys Lys Leu Trp Gln Tyr Asp Ala Arg Leu Pro Asp Asp Ile
        115                 120                 125

Arg Pro Cys Cys Asp Val Ile Asn Arg Gly Val Ala Leu Tyr Gly Asn
    130                 135                 140
```

```
Leu Val Phe Phe Gly Thr Leu Asp Ala Lys Leu Val Ala Leu Asn Lys
145                 150                 155                 160

Asp Thr Gly Lys Val Trp Ser Lys Lys Val Ala Asp His Lys Glu
            165                 170                 175

Gly Tyr Ser Ile Ser Ala Ala Pro Met Ile Val Asn Gly Lys Leu Ile
                180                 185                 190

Thr Gly Val Ala Gly Gly Glu Phe Gly Val Val Gly Lys Ile Gln Ala
            195                 200                 205

Tyr Asn Pro Glu Asn Gly Glu Leu Leu Trp Met Arg Pro Thr Val Glu
210                 215                 220

Gly His Met Gly Tyr Val Tyr Lys Asp Gly Lys Ala Ile Glu Asn Gly
225                 230                 235                 240

Ile Ser Gly Gly Glu Ala Gly Lys Thr Trp Pro Gly Asp Leu Trp Lys
                245                 250                 255

Thr Gly Gly Ala Ala Pro Trp Leu Gly Gly Tyr Tyr Asp Pro Glu Thr
            260                 265                 270

Asn Leu Ile Leu Phe Gly Thr Gly Asn Pro Ala Pro Trp Asn Ser His
            275                 280                 285

Leu Arg Pro Gly Asp Asn Leu Tyr Ser Ser Arg Leu Ala Leu Asn
290                 295                 300

Pro Asp Asp Gly Thr Ile Lys Trp His Phe Gln Ser Thr Pro His Asp
305                 310                 315                 320

Gly Trp Asp Phe Asp Gly Val Asn Glu Leu Ile Ser Phe Asn Tyr Lys
                325                 330                 335

Asp Gly Gly Lys Glu Val Lys Ala Ala Thr Ala Asp Arg Asn Gly
            340                 345                 350

Phe Phe Tyr Val Leu Asp Arg Thr Asn Gly Lys Phe Ile Arg Gly Phe
            355                 360                 365

Pro Phe Val Asp Lys Ile Thr Trp Ala Thr Gly Leu Asp Lys Asp Gly
            370                 375                 380

Arg Pro Ile Tyr Asn Asp Ala Ser Arg Pro Gly Ala Pro Gly Ser Glu
385                 390                 395                 400

Ala Lys Gly Ser Ser Val Phe Val Ala Pro Ala Phe Leu Gly Ala Lys
                405                 410                 415

Asn Trp Met Pro Met Ala Tyr Asn Lys Asp Thr Gly Leu Phe Tyr Val
            420                 425                 430

Pro Ser Asn Glu Trp Gly Met Asp Ile Trp Asn Glu Gly Ile Ala Tyr
            435                 440                 445

Lys Lys Gly Ala Ala Phe Leu Gly Ala Gly Phe Thr Ile Lys Pro Leu
            450                 455                 460

Asn Glu Asp Tyr Ile Gly Val Leu Arg Ala Ile Asp Pro Val Ser Gly
465                 470                 475                 480

Lys Glu Val Trp Arg His Lys Asn Tyr Ala Pro Leu Trp Gly Gly Val
                485                 490                 495

Leu Thr Thr Lys Gly Asn Leu Val Phe Thr Gly Thr Pro Glu Gly Phe
            500                 505                 510

Leu Gln Ala Phe Asn Ala Lys Thr Gly Asp Lys Val Trp Glu Phe Gln
            515                 520                 525

Thr Gly Ser Gly Val Leu Gly Ser Pro Val Thr Trp Glu Met Asp Gly
            530                 535                 540

Glu Gln Tyr Val Ser Val Ser Gly Trp Gly Gly Ala Val Pro Leu
545                 550                 555                 560
```

Trp Gly Gly Glu Val Ala Lys Arg Val Lys Asp Phe Asn Gln Gly Gly
            565                 570                 575

Met Leu Trp Thr Phe Lys Leu Pro Lys Gln Leu Gln Gln Thr Ala Ser
        580                 585                 590

Val Lys Pro
        595

<210> SEQ ID NO 36
<211> LENGTH: 1000
<212> TYPE: DNA
<213> ORGANISM: Artificial Sequence
<220> FEATURE:
<223> OTHER INFORMATION: Oligonucleotide

<400> SEQUENCE: 36
ccgtggagcc cagcagcaat gccaggccgt gacggccatg gctgccgaca acgatcaggt        60
cgcacttctg gtccttggcc aactggtgga tttcctggcg aggctggccg taggtcaggt       120
gcgagtcgcc gcggttgatt gccgggtatt tattgaacag gcggtccatg cgctccttgg       180
cctggtcgaa ctgctgctgt tgcagctgcg acaggtccat cggtacgtca ccgccgaagg       240
ccatggccat cggctcgacg atgtgcacca gggatacctt ggctttcgaa ggctctgcca       300
gcgccatggc gcgcttgatc accgggtcgc attcttcggt caggtcgacg gcgaccaaca       360
aatgttcgta ttcatgagcg gtactcctgc acaatcgcga tagaagaagt atggtcgctt       420
tagggcgggt ctaccgtgaa aaatggctaa ccagctcatt gcaacgcttt atgggaact        480
actgatatga cggtattgct ggtggtgtca atccttgcgc tgattctcag cccgctttcc       540
tggctgcgca gctcgcgcaa gcagagcgag cagatgaagt tgcgcctgga ggcgcggcgc       600
atgggtttgg ccatgcaact ggcgccgcag cagtggccgc actggctgga aaaggagccg       660
ccaagcccct gcccgcagta tcacagagcc cggcgccgtg ggcatgagga cagcttcagc       720
ttctggcagg tcagccccgg agtgtggtgg aaccagtggc gcgagccctg cgaagaccca       780
cgtttcatgg gcgcgttgtc gcgcttgccg gcgagtgtgt acaaggtcga ggccgatgcg       840
cggatgattg ccctgtactg gaccgaacgt ggcgatactg ctgtgttgca ggatgttgcc       900
tacgccctcg aaaccttggc ttgagcgccg cccatacgcg acccctgtag gcgcggattc       960
atctgcgaac actggcagag ccggtgccaa actccgcggt                            1000

<210> SEQ ID NO 37
<211> LENGTH: 995
<212> TYPE: DNA
<213> ORGANISM: Artificial Sequence
<220> FEATURE:
<223> OTHER INFORMATION: Oligonucleotide

<400> SEQUENCE: 37
tcgcgtagcg ggacagcagc cggggcctag tgccccggtt ttgttttttc aggttttttt        60
caggaggtgt gcaacatgca gatacaacca ggcgtatacc ggcattacaa agggcctgag       120
taccgtgtct tcagtgttgc gcggcactcc gaaaccgaag agtggatggt gttctaccaa       180
tgcctgtatg gtgattacag cttctgggtg cgtcccctt cgatgttcca ggagtccgtc        240
gaatttgacg cgagcaggt gccacgcttt gctttggtca aggccgaaga ggggctgccc       300
gggttgctgg gcaagtcgca cgcgtgatcg tccgagcttg acctcacact tttgccacta       360
tatatagcgg tgccgcgtct ggcacttggc gcgtttttta tcttcagatt caggaatact       420
ccgatccatg ggcaaatcgc tggtcattgt ggaatccccg gccaaggcca agaccatcaa       480

```
caagtacctg ggcaaccagt acgtggtgaa gtcgagtatc ggccatatcc gagacctccc    540
caccagcggt tcggccagcg cgagcaaaga gccggccgcc aagcgtggca aggctgcggg    600
tgaggcgccg gcgctttcgc cgaaagagaa ggcccgccgc cagctggtgg cacgcatggg    660
cgtcgacccc gaccatggct ggaaggccaa gtacgagatc ctgcctggca aggaaaaggt    720
gatcgaagag ctgcgccgcc tggccaagga tgccgacacc atctacctcg caaccgactt    780
ggaccgcgaa ggggaagcca ttgcctggca cctgcgcgag gccatcgggg gtgacgacac    840
ccgctacaag cgcgtggtgt tcaacgaaat taccaagaag gccattcagg aagccttctc    900
gcagccaggc gagctggaca tcgaccgggt caatgcccag caggcgcggc gtttcctcga    960
ccgcgtggtc ggttacatgg tttcgccact gctgt                               995

<210> SEQ ID NO 38
<211> LENGTH: 1000
<212> TYPE: DNA
<213> ORGANISM: Artificial Sequence
<220> FEATURE:
<223> OTHER INFORMATION: Oligonucleotide

<400> SEQUENCE: 38
caggtcagct cacacgccga gcttgtgcat ctggggattg atctgggggt ggtgcgggtg     60
gcggggtgag gtatttcatt gcacctgttg gggctgcgtc gcagccgacc gcgcccaacg    120
gaatgtatcc acccccgac atgtgtccac ccccgaatca ggcgtaggag cgggtttacc     180
cgcgaatacg gtggcggcgg caacggtgaa tagcgggtgg aaattggcca gcagggccgg    240
cccttttcgcg ggtaaacccg cgcctacagg cccctcattt gtcccaggtc tcagggcacc   300
ccttgcaccc ctccatgttg gcctcctgaa aattcccgta atgctgccgt gccccgcgta    360
aatcggcgtg tgccaggttg ctctggccaa acttggcctc ctgcaggttg gcatccccca    420
ggttggcctc ttgcaggtca gccttgctca accaggccat ctccaggtcc gccgcctgca    480
agttggcctg ctgcagcttt gccccggaca gcctggcgaa ctgcagatag gctgcgcgca    540
ggtccgcctt ttcaaactgt gcgccctggg cgaacaagcc ccagccttga atggccacca    600
gcctgctgtt gctcaggtca gccaggcgca gattgctctg ttgcaggctg gcgcgggtca    660
ggttggctcc ttgcaggcgg gcttttttcca gatttgcgag gtccagctgg catgacgca    720
ggtcggcatc gcgcaggtcg gcaccggcca ggttcatctt gcgcaggtcc tggttggcca    780
ggttggcgcc gcgcaggttg gccccgggc actggctggc ttcggcaatc acgcagccgt    840
tgatggtcaa gggggtatcg gtgccggcgt cgtcggcgtt cactgccagg caggggata    900
gcgccagcag caaggtcaag ggcaggtaat tcatggcaaa agcctctgga cgggagaagg    960
gcagaaacgg ggaggggcgc aggccgctcc ccgctgcagg                         1000

<210> SEQ ID NO 39
<211> LENGTH: 1000
<212> TYPE: DNA
<213> ORGANISM: Artificial Sequence
<220> FEATURE:
<223> OTHER INFORMATION: Oligonucleotide

<400> SEQUENCE: 39
ggttgcagtt cccagtggag gttttggcct gcacagggtg gggcgcagcg gccatcgcgg     60
gatacggaaa aagtcccgcc cttgccggga ataattcccg cgcggcacct caattggccc    120
ttcgccacaa gccctactac caagggatta aggcccggcc accaaagcag cattcggccg    180
cccgcgggct gttcctaaga tgcggcacg gcctctgtgg ttgaggcttt gtgtgcaatg    240
```

```
gtgagggcat aacaatgaca acaaaatgca atgtgttgct tgctgctggg ttgctggccg      300
cagccgtgct gaccggtaca gcctgggccc atggcaacgt ggtgcccag gcagtggaga      360 ccaagggcct gaccccgatc aaggacactg gcgtgagcct ggacggcgac ggctgggccg      420
cggtcaaccc gtaccgcagc tcgcccgagc acgacaaggc cgtggaaatc ggcgcctcgg      480
cctacaacca gaactgcgct gcctgtcatg gcctggaggc caagtccggt ggtatcgcgc      540
ctgacttgcg catgctcgat gcgggtgatg ccggcgatga atggttcgtc gagcgggtac      600
gccacggcgc ggttcgcgac ggccgcgtgt acatgccgaa gatggccgat acctcagcc      660 aggaagccct gtgggcggtg cgcacctatc tggacagcgt gcacgtcgag gagtgacggc      720
catgcgtctg tgggcggtgc tgttgagtgg cctgctgctg tggtgcgcgg cggcccaggc      780
gcaggtgcgc aactatgacg cgatcatcgc tgccggcgag ctcaaggtgg cggtgtacaa      840
ggatttcgcc ccctacagtt ttcaggacca cggccagccg cgtggtgtcg atgtggagct      900
ggcgcaggcc ctggccacgg ccttgggggt acgcctgcaa ctgatctggg cgccacccgg      960
agaaaagctc gacgatgacc tgcgcgacta catctggcgt                         1000
```

```
<210> SEQ ID NO 40
<211> LENGTH: 978
<212> TYPE: DNA
<213> ORGANISM: Artificial Sequence
<220> FEATURE:
<223> OTHER INFORMATION: Oligonucleotide

<400> SEQUENCE: 40
```

```
ctggttgctg gaaggcagca ccgacaattt cgccaaggcc aatggcggca atgtggtcaa       60
caccgcgttc atcgtcaccg acagcggtgt ggtggtgatc gacagcgggc cgtcgaaagg      120
ctatggcgag gcattgcgca aggcaattgc caccctcacc gacaagccgg tagtggaggt      180
gctgctgacc catcatcatc ctgaccatgt gctgggcaac caggcctttg ccgatgtgcc      240
gatcggtgcc ctggccggca cccgcgacct gctgcgccag caaggcgatg ccatggccga      300
gaacatgtat cgcctggtcg gcgactggat gcgcggtacc gaggtggtgc tgccgacccg      360
ggtgctgcag ccgggcgtgc atgaggtggg tgggcaccgc ctgaggttgc tggggctggg      420
cgggcatacg ggtgccgacc tggcgatttt cgatgaaaag accggggtgc tgttcgccgg      480
cgacctggtg ttctaccaac gcgccctgac cacgcccaac agcccggggc tggacgtgtg      540
gctcaaggac ctggataccc tgcaggcact gccctggaaa cagcttgtac ccgggcatgg      600
cccgttggcc agtgatgcgc agccgttcgt gcagatgcgt gactacctgg gctggctcga      660
tggcctgatg cgtgatggcg cggcgcgcgg tgacgacatg gctgagatga tccgcagccc      720
cattcccgaa cgttttgccg ggatcagcct gacgcgttat gagctgatcc gcagtgtcag      780
ccacctgtac ccgcgttacg agcgccagca gttgcagcgc ttgccatgac atttttttgtg      840 cctgtcagcc cccgtgccgc ccacccatca ctcaggccgc taccaaggaa ctagaaaact      900
ccgcactgcg agcaattgtt ggcaatcggg tcgggaccaa gaattcccga cacaccggga      960 aatttttcccg ggcacaac                                                   978
```

```
<210> SEQ ID NO 41
<211> LENGTH: 1000
<212> TYPE: DNA
<213> ORGANISM: Artificial Sequence
<220> FEATURE:
<223> OTHER INFORMATION: Oligonucleotide
```

-continued

```
<400> SEQUENCE: 41
accgcgtcgc ggccttcgcg ggcttgcccg ctcccacagg ttcaccgctg gttccagaac      60
cggtgaagaa cctgtgggggg cgggcgagcc cgcaaaaggg ccggcacatg catggcctac    120
ccgtaccaac gcaccccgca agctcgttcc aaagtagcat tcggtccagt ccgcccccgt    180
gcattaatgc ttctaccgga atcctccggc acaagaagag gacttgccct atgtggacta    240
aacccgccta taccgacctg cgcattggct tcgaagtgac gatgtatttc gccaaccgtt    300
gatgacggcc cggccatcgc cacggtggcc ggatcctcct ggagtatgcg cctgtgaacc    360
tgattgatcg ccagcaggcc cttgccttgg ggcgaggctt cgcctggac tgggagccac    420
ggaaggcttg ccacgtgctg ttgtacgccg ggggcatcat cgagctcaat gccagtgccg    480
gctgggtcct cgagctgctg gacggccaca gtaccgtggc aacggtcatc gaccgcctgg    540
cacaacgctt ccccaatgta ccggggctcg aagaggacgt actggcgttt ctggaggtgg    600
cccgcgccaa atcctggata gaatgaccgg tagccccgct ttggtctggt tgctttcgtg    660
gtgggatgct ttacgctggc ggttatcttc cagaacaata agaacaggct taccgatgag    720
ccagagtttc agccccccttc gcaagttcgt atcgcctgaa atcatctttg gtgccggctg    780
ccggcacaat gtgccaatt acgccaaaac cttcggtgcg cgcaaggtac tggtggtcag    840
cgaccctggc gtgatcgccg ccggctgggt ggcggatgtg gaggccagcc tgcaggccca    900
gggtatcgac tactgcctgt acacagcggt gtcacccaac ccgcgggtcg aggaggtgat    960
gctcggcgcc gagatctatc ggcagaacca ctgtgacgtg                         1000

<210> SEQ ID NO 42
<211> LENGTH: 774
<212> TYPE: DNA
<213> ORGANISM: Artificial Sequence
<220> FEATURE:
<223> OTHER INFORMATION: Oligonucleotide

<400> SEQUENCE: 42
cacatcgact cggctattca tcatcccctc cggaatttaa ttagcaccct aacgataaag      60
ccatgatacg cctgacagtg gtgcggaaac agcgcattgc ggtacagcag tgtttcgtaa    120
ggcgcaacaa aaacggtctc gtcgagaaac gcaaaaagcc ccagggatag ctccgagggg    180
cttggcacca cgcgcggttt tatacctggc gctggtggcg gtcgagctgc tcgtggcgct    240
cctgagcttc gatgcagtac ttggtggtcg ggctgatcag caaacgcttc aggccgatgg    300
gctcaccact gtcatcgcac cagccgaagc tttcgtcggc aatacggtcc agggccattt    360
caagctgtgg cagcaggcgc tggtcgcggt cgatggcatt taccagccag ctacgttctt    420
cttcgaccga agccacgtcg gcagggtctg acggagtgtc caggccttcg atggtggtgc    480
ggctgagttc gatgcgttca tgggtttcga cttcatcgc ctgcagcagc tcagtaaaga    540
aggcaagctg gtcggcgttc atgtagtcat cggccgacat ggccagcaac tgttccttgg    600
tcatcgattt ctctatgaaa aaatgtgcat ttgggcgatt catgtgccgt cgatgcctat    660
gcatcgccag cggaattctt caagcgccaa ccggcactct tttacagggg cggcagtct    720
aaggcgccac gccgcgtgga gcaactgcaa atgggtgcga atttgcttcc actg         774

<210> SEQ ID NO 43
<211> LENGTH: 849
<212> TYPE: DNA
<213> ORGANISM: Artificial Sequence
<220> FEATURE:
<223> OTHER INFORMATION: Oligonucleotide
```

<400> SEQUENCE: 43

```
agctgggtat caccaacctg gccggctcgc ccaccgcgta tcgcttgctg attgcggcgg      60
gcaaagattt ctcggcaccg atcaagggcc gcctgcgggt ggtcagcagt gccggcgaac     120
cgctgaaccc cgaagtgatc cgctggttcg ccgacgagct gggcgtgacc attcacgatc     180
actacggcca gaccgaactg gcatggtgc tgtgcaacca ccatggcctg cagcatccgg      240
tgcacctggg ttctgccggc tatgccatcc ccggccaccg catcgtggtg gtggacgagc     300
aaggtaacga actgccagcc ggccagccag gcatcctcgc cgttgaccgt gagcagtcgc     360
cgctgtgctg gttcggcggt taccacggcc tgccgaccaa agccttcgtc ggcaagtact     420
acctcagcgg cgacactgtc gagctgaacc cggatggcag catcagcttc gttggccgta     480
gcgacgacgt gatcaccacc tccggttacc gtgtggggcc attcgatgtg aaagcgcgt      540
tgatcgagca cccggcggtg atcgaggcag cggtgatcgg caagcccgac ccggagcgta     600
ccgagctgat caaggcgttc gtggtattgg ccagcggcta cgccggcagc gtcgagctgg     660
aagaaacctt gcgccagcat gtgcgccagc gcctctacgc gcatgcctac cccagggaaa     720
tcgaattcgt cagcgagctg cccaagaccc gagcggcaa gctgcaacgc ttcatcctgc      780
gcaaccagga agtcgccaaa caacaagcgc aacaggccac ccctgccagc gtctgaaagg     840
aaagtactc                                                             849
```

<210> SEQ ID NO 44
<211> LENGTH: 1000
<212> TYPE: DNA
<213> ORGANISM: Artificial Sequence
<220> FEATURE:
<223> OTHER INFORMATION: Oligonucleotide

<400> SEQUENCE: 44

```
gaccgaaaac atcggtgccc gccgcctgca caccctgctc gagcgtttgc tcgaagaagt      60
gtcgttcagt gcgggcgacc tggccagcac ccatgacgaa gcgccgatcc agatcgacgc     120
ggcgtatgtg aacagccacc tgggtgagct ggcacagaac gaagacctgt cgcgttacat     180
tctgtaagac cggtttcgac agtttcgcgg gcaagcccgc tcctgcacgc gccaccacaa     240
cccttgggcc tgtggtgatc cgtgcggggg cgggcttgcc cgcgaagagg cccttgaatc     300
cctccccat aagctggaag ctgtgcttca tcagctcccg agagattctg cccatggccc      360
gcctgcctac cgccatcaac ctgcacaaag cctccaagac cctcagcctc acctacgcac     420
ccggcgaggt ctaccacctg cccgccgaat tcctgcgcgt gcactctccc tccgccgagg     480
tccagggcca cggcaacccc atcctgcagt tcggcaagat caacgtcggc ctcagtggct     540
tggaacctgc cggccaatat gcactgaaac tgaccttcga cgacgccat gacagcggct      600
tgttcacttg ggaatacctt gagcaactgt gcctgcgcca ggaacaactg tgggcagaat     660
acctcgatga gttgcaaaag gccggcaaat cccgcgaccc agccgaatct gtggtcaagc     720
tcatgctcta gcgcaaggcc tgcggggttt agagcgcatt ttctaaattc atctgtttga     780
atgacttgca gacagcccag tgaagggctg tcttgcgcat tacacgaaag tcgggtaacc     840
aatgggtgtg gcaagttccc tgcatgactt tgcaggtcgg cagaacccac gcagcaccgc     900
tgttccttat cactggtcac ccgagtagca gtaccgggct cagggctgtg cacccgccac     960
agcaaccggt actcgtctca ggacaacgga gcgtcgtaga                          1000
```

<210> SEQ ID NO 45

```
<211> LENGTH: 975
<212> TYPE: DNA
<213> ORGANISM: Artificial Sequence
<220> FEATURE:
<223> OTHER INFORMATION: Oligonucleotide

<400> SEQUENCE: 45
gctgctgact ggatgaaaac ccgcgatcgt atccttgaat gcgccctgca gttgttcaac      60
cagcagggcg aacccaacgt atccaccctg gaaattgcca acgaactcgg catcagccca     120
ggcaacctgt actaccactt ccatggcaag gagcccttgg ttctgggctt gttcgagcgt     180
tttgaagaag cgttgatgcc gttgctggac ccaccgctgg aggtgcggct ggacgcagag     240
gattactggc tgtttctgca cttgatcgtc gagcgcatgg ctcagtaccg cttcctgttc     300
caggacctgt ccaacctgac cgggcgcctg cccaaactcg cccgaggcat gcgcagcctg     360
atcaatgcaa tcaaacgcac gctggcggcg ctgttggcca gcctcaagag ccaggggctg     420
gtagaaagtg atacccaggc gctggggcaa ctggtcgagc agatcacact gacgctgatg     480
ttctcgctgg attaccagcg tgtgctgggg cgcgaggggg atgtggggat cgtggtgtat     540
caggtgatga tgctggtggc gccgcatctg caggcccagg cccgggcggc ggcggagcag     600
ctggcagtga agtacctgga ggggtaggcc tgctggagat gtagtgttgc agccgacgca     660
ttcgcgggta aacccgctcc tacaaggttt ggcgcatctt gtaggagcgg gtttacccgc     720
gaagaaggcg acgcggtatc agatcagggt accggtgcca gtcggtgccg acggcgtgct     780
gctggccggg gtggcggcag ttgccggtgc tgtggtcgct gcaggcgcag cgctggcagc     840
tggtgctgct ggtttggccg ctgccggttt ggctggagct ttcttcaccg caggtttctt     900
ggctgccgca ggtttggccg ctgcaggctt ggctgctggc ttagctgcag gttttccgc     960 tgcggttttg gctgc                                                     975
```